(12) United States Patent
Chetham

(10) Patent No.: US 8,068,906 B2
(45) Date of Patent: Nov. 29, 2011

(54) CARDIAC MONITORING SYSTEM

(75) Inventor: Scott Matthew Chetham, Del Mar, CA (US)

(73) Assignee: Aorora Technologies Pty Ltd, Eight Mile Plains, QLD (AU)

( * ) Notice: Subject to any disclaimer, the term of this patent is extended or adjusted under 35 U.S.C. 154(b) by 711 days.

(21) Appl. No.: 11/776,456

(22) Filed: Jul. 11, 2007

(65) Prior Publication Data

US 2008/0009759 A1 Jan. 10, 2008

Related U.S. Application Data

(63) Continuation-in-part of application No. 11/629,804, filed as application No. PCT/AU2005/000893 on Jun. 21, 2005, now abandoned.

(30) Foreign Application Priority Data

Jun. 21, 2004 (AU) ................................. 2004903334
Oct. 26, 2004 (AU) ................................. 2004906181

(51) Int. Cl.
*A61B 5/05* (2006.01)
*A61B 5/02* (2006.01)
*A61B 5/08* (2006.01)

(52) U.S. Cl. ......... 600/547; 600/481; 600/484; 600/508

(58) Field of Classification Search .................. 600/481, 600/484, 506, 508, 509, 529, 533, 536, 547
See application file for complete search history.

(56) References Cited

U.S. PATENT DOCUMENTS

| | | | |
|---|---|---|---|
| 3,316,896 A | 5/1967 | Thomasset | |
| 3,851,641 A | 12/1974 | Toole et al. | |
| RE30,101 E | 9/1979 | Kubicek et al. | |
| 4,450,527 A | 5/1984 | Sramek | |
| 4,486,835 A | 12/1984 | Bai et al. | |
| 4,890,630 A | 1/1990 | Kroll et al. | |

(Continued)

FOREIGN PATENT DOCUMENTS

CN 1180513 A 5/1998

(Continued)

OTHER PUBLICATIONS

Chetham, Matthew; U.S. Appl. No. 11/629,804 entitled "Cardiac monitoring system," filed Dec. 15, 2006.

(Continued)

*Primary Examiner* — Max Hindenburg
*Assistant Examiner* — Devin Henson
(74) *Attorney, Agent, or Firm* — Shay Glenn LLP

(57) ABSTRACT

A method of analyzing cardiac functions in a subject using a processing system is described. The method may include applying one or more electrical signals having a plurality of frequencies to the subject and detecting a response to the applied one or more signals from the subject. A characteristic frequency can then be determined from the applied and received signals, and at least one component of the impedance (e.g., reactance, phase shift) can be measured at the characteristic frequency. Thus, the impedance or a component of impedance at a characteristic frequency can be determined for a number of sequential time instances. A new characteristic frequency may be determined within a cardiac cycle (e.g., with each sequential time instant) or the same characteristic frequency may be used throughout the cardiac cycle during which instantaneous values of impedance (or a component of impedance) are determined. These instantaneous values may be used to determine one or more indicia of cardiac function.

24 Claims, 10 Drawing Sheets

U.S. PATENT DOCUMENTS

| | | |
|---|---|---|
| 4,905,705 A | 3/1990 | Kizakevich et al. |
| 4,924,875 A | 5/1990 | Chamoun |
| 5,063,937 A | 11/1991 | Ezenwa et al. |
| 5,086,781 A * | 2/1992 | Bookspan .................... 600/547 |
| 5,101,828 A | 4/1992 | Welkowitz et al. |
| 5,280,429 A | 1/1994 | Withers |
| 5,309,917 A | 5/1994 | Wang et al. |
| 5,423,326 A | 6/1995 | Wang et al. |
| 5,449,000 A | 9/1995 | Libke et al. |
| 5,454,377 A | 10/1995 | Dzwonczyk et al. |
| 5,469,859 A | 11/1995 | Tsoglin et al. |
| 5,503,157 A | 4/1996 | Sramek et al. |
| 5,526,808 A | 6/1996 | Kaminsky |
| 5,529,072 A | 6/1996 | Sramek |
| 5,626,146 A | 5/1997 | Barber et al. |
| 5,732,710 A | 3/1998 | Rabinovich et al. |
| 5,735,284 A | 4/1998 | Tsoglin et al. |
| 5,746,214 A | 5/1998 | Brown et al. |
| 5,759,159 A | 6/1998 | Masreliez |
| 5,788,643 A | 8/1998 | Feldman |
| 5,807,272 A | 9/1998 | Kun et al. |
| 5,876,353 A | 3/1999 | Riff |
| 5,957,861 A | 9/1999 | Combs et al. |
| 6,018,677 A | 1/2000 | Vidrine et al. |
| 6,125,297 A | 9/2000 | Siconolfi |
| 6,151,523 A | 11/2000 | Rosell Ferrer et al. |
| 6,208,890 B1 | 3/2001 | Sarrazin et al. |
| 6,339,722 B1 | 1/2002 | Heethaar et al. |
| 6,469,732 B1 | 10/2002 | Chang et al. |
| 6,472,888 B2 | 10/2002 | Oguma et al. |
| 6,496,725 B2 | 12/2002 | Kamada et al. |
| 6,511,438 B2 | 1/2003 | Bernstein et al. |
| 6,512,949 B1 | 1/2003 | Combs et al. |
| 6,532,384 B1 | 3/2003 | Fukuda et al. |
| 6,551,252 B2 | 4/2003 | Sackner et al. |
| 6,556,001 B1 | 4/2003 | Wiegand et al. |
| 6,560,480 B1 | 5/2003 | Nachaliel et al. |
| 6,561,986 B2 | 5/2003 | Baura et al. |
| 6,602,201 B1 | 8/2003 | Hepp et al. |
| 6,615,077 B1 | 9/2003 | Zhu et al. |
| 6,631,292 B1 | 10/2003 | Liedtke |
| 6,636,754 B1 | 10/2003 | Baura et al. |
| 6,643,543 B2 | 11/2003 | Takehara et al. |
| 6,714,813 B2 | 3/2004 | Ishigooka et al. |
| 6,724,200 B2 | 4/2004 | Fukuda |
| 6,725,089 B2 | 4/2004 | Komatsu et al. |
| 6,760,617 B2 | 7/2004 | Ward et al. |
| 6,790,178 B1 | 9/2004 | Mault et al. |
| 6,807,443 B2 | 10/2004 | Keren |
| 6,829,501 B2 | 12/2004 | Nielsen et al. |
| 6,829,503 B2 | 12/2004 | Alt |
| 6,980,852 B2 | 12/2005 | Jersey-Willuhn et al. |
| 7,096,061 B2 | 8/2006 | Arad |
| 7,122,012 B2 | 10/2006 | Bouton et al. |
| 7,149,573 B2 | 12/2006 | Wang |
| 7,169,107 B2 | 1/2007 | Jersey-Willuhn et al. |
| 7,184,820 B2 | 2/2007 | Jersey-Willuhn et al. |
| 7,184,821 B2 | 2/2007 | Belalcazar et al. |
| 7,186,220 B2 | 3/2007 | Stahmann et al. |
| 7,233,823 B2 | 6/2007 | Simond et al. |
| 7,251,524 B1 | 7/2007 | Hepp et al. |
| 2001/0051774 A1 | 12/2001 | Littrup et al. |
| 2002/0138019 A1 | 9/2002 | Wexler et al. |
| 2003/0023184 A1 | 1/2003 | Pitts-crick et al. |
| 2003/0028221 A1 | 2/2003 | Zhu et al. |
| 2003/0105411 A1 | 6/2003 | Smallwood et al. |
| 2003/0120170 A1 | 6/2003 | Zhu et al. |
| 2003/0120182 A1 | 6/2003 | Wilkinson et al. |
| 2003/0173976 A1 | 9/2003 | Wiegand et al. |
| 2003/0216664 A1 | 11/2003 | Suarez |
| 2004/0015095 A1 | 1/2004 | Li et al. |
| 2004/0019292 A1 | 1/2004 | Drinan et al. |
| 2004/0073130 A1 | 4/2004 | Bohm et al. |
| 2004/0116819 A1 | 6/2004 | Alt et al. |
| 2004/0158167 A1 | 8/2004 | Smith et al. |
| 2004/0167423 A1 | 8/2004 | Pillon et al. |
| 2004/0234113 A1 | 11/2004 | Miga |
| 2004/0236202 A1 | 11/2004 | Burton |
| 2004/0242989 A1 | 12/2004 | Zhu et al. |
| 2004/0260167 A1 | 12/2004 | Leonhardt et al. |
| 2005/0039763 A1 | 2/2005 | Kraemer et al. |
| 2005/0070778 A1 | 3/2005 | Lackey et al. |
| 2005/0080460 A1 | 4/2005 | Wang et al. |
| 2005/0101875 A1 | 5/2005 | Semler et al. |
| 2005/0107719 A1 | 5/2005 | Arad |
| 2005/0177062 A1* | 8/2005 | Skrabal et al. ............... 600/547 |
| 2005/0192488 A1* | 9/2005 | Bryenton et al. ............ 600/301 |
| 2005/0201598 A1 | 9/2005 | Harel et al. |
| 2005/0203435 A1 | 9/2005 | Nakada |
| 2005/0215918 A1 | 9/2005 | Frantz et al. |
| 2005/0228309 A1 | 10/2005 | Fisher |
| 2005/0261743 A1 | 11/2005 | Kroll et al. |
| 2005/0283091 A1 | 12/2005 | Kink et al. |
| 2006/0004300 A1* | 1/2006 | Kennedy ...................... 600/547 |
| 2006/0041280 A1 | 2/2006 | Stahmann et al. |
| 2006/0064029 A1 | 3/2006 | Arad |
| 2006/0085049 A1 | 4/2006 | Cory et al. |
| 2006/0122540 A1 | 6/2006 | Zhu et al. |
| 2006/0135886 A1 | 6/2006 | Lippert et al. |
| 2006/0200033 A1 | 9/2006 | Keren et al. |
| 2006/0224079 A1 | 10/2006 | Washchuk |
| 2006/0241513 A1 | 10/2006 | Hatlestad et al. |
| 2006/0241719 A1 | 10/2006 | Foster et al. |
| 2006/0247543 A1* | 11/2006 | Cornish et al. ............... 600/508 |
| 2006/0258952 A1 | 11/2006 | Stahmann et al. |
| 2006/0264775 A1 | 11/2006 | Mills et al. |
| 2006/0264776 A1 | 11/2006 | Stahmann et al. |
| 2006/0293609 A1 | 12/2006 | Stahmann et al. |
| 2007/0007975 A1 | 1/2007 | Hawkins et al. |
| 2007/0010758 A1 | 1/2007 | Matthiessen et al. |
| 2007/0027402 A1 | 2/2007 | Levin et al. |
| 2007/0049993 A1 | 3/2007 | Hofmann et al. |
| 2007/0156061 A1 | 7/2007 | Hess |
| 2008/0001608 A1 | 1/2008 | Saulnier et al. |
| 2008/0064981 A1 | 3/2008 | Gregory |
| 2008/0252304 A1 | 10/2008 | Woo et al. |
| 2008/0319336 A1 | 12/2008 | Ward et al. |
| 2009/0084674 A1 | 4/2009 | Holzhacker et al. |

FOREIGN PATENT DOCUMENTS

| | | |
|---|---|---|
| CN | 1236597 A | 12/1999 |
| CN | 1329875 A | 1/2002 |
| EP | 0581073 A2 | 2/1994 |
| EP | 0339471 B1 | 3/1997 |
| EP | 0865763 A2 | 9/1998 |
| EP | 1078597 A2 | 2/2001 |
| EP | 1112715 A1 | 7/2001 |
| EP | 1238630 A2 | 9/2002 |
| EP | 1247487 A1 | 10/2002 |
| EP | 1329190 A1 | 7/2003 |
| EP | 1080686 B1 | 3/2004 |
| FR | 2748928 A1 | 11/1997 |
| JP | 06-000168 A | 1/1994 |
| JP | 08-191808 A | 7/1996 |
| JP | 09-051884 A | 2/1997 |
| JP | 09-220209 A | 8/1997 |
| JP | 10-000185 A | 1/1998 |
| JP | 2000-107138 A | 4/2000 |
| JP | 2000-139867 A | 5/2000 |
| JP | 2001037735 A | 2/2001 |
| JP | 2001061804 A | 3/2001 |
| JP | 2003-2116805 A | 4/2003 |
| RU | 2112416 C1 | 6/1998 |
| RU | 2138193 C1 | 9/1999 |
| WO | WO 93/18821 A1 | 9/1993 |
| WO | WO 96/01586 A1 | 1/1996 |
| WO | WO 97/11638 A2 | 4/1997 |
| WO | WO 98/06328 A1 | 2/1998 |
| WO | WO98/33553 A1 | 8/1998 |
| WO | WO 98/51211 A1 | 11/1998 |
| WO | WO 00/40955 A1 | 7/2000 |
| WO | WO00/79255 A1 | 12/2000 |
| WO | WO 01/27605 A1 | 4/2001 |
| WO | WO 2004/030535 A1 | 4/2004 |
| WO | WO 2004/032738 A1 | 4/2004 |
| WO | WO 2004/047638 A1 | 6/2004 |

| WO | WO 2005/018432 A2 | 3/2005 |
| WO | WO 2005/122881 A1 | 12/2005 |
| WO | WO 2005/122888 A1 | 12/2005 |

OTHER PUBLICATIONS

Chetham, Matthew; U.S. Appl. No. 11/993,842 entitled "Pulmonary monitoring system," filed Dec. 21, 2007.

Chetham, Matthew; U.S. Appl. No. 11/996,065 entitled "Index determination," filed Jan. 19, 2008.

Bella et al., "Relations of left ventrical mass to fat-free and adipose body mass: the strong heart study," Circulation, vol. 98, pp. 2538-2544, Dec. 8, 1998.

Ellis, K.J. et al., "Human hydrometry: comparison of multifrequency bioelectrical impedance with 2H2O and bromine dilution," Journal of Applied Physiology, vol. 85, No. 3, pp. 1056-1062, 1998.

Iacobellis et al., "Influence of excess fat on cardiac morphology and function: study in uncomplicated obesity," Obesity Research, vol. 10, No. 8, pp. 767-773, Aug. 8, 2002.

Jones, C.H. et al., "Extracellular fluid volume determined by bioelectric impedance and serum albumin in CAPD Patients," Nephrology Dialysis Transplantation, vol. 13, pp. 393-397, 1998.

Thomas, B.J., "Future Technologies," Asia Pacific Journal Clinical Nutrition, vol. 4, pp. 157-159, 1995.

Woodrow, G. et al., "Effects of icodextrin in automated peritoneal dialysis on blood pressure and bioelectrical impedance analysis," Nephrology Dialysis Transplantation, vol. 15, pp. 862-866, 2000.

Yoshinaga et al., "Effect of total adipose weight and systemic hypertension on left ventrical mass in children," American Journal of Cardiology, vol. 76, pp. 785-787, Oct. 15, 1995.

Karason et al., "Impact of blood pressure and insulin on the relationship between body fat and left ventricular structure," European Heart Journal, vol. 24, pp. 1500-1505, 2003.

Bernstein; "A new stroke volume equation for thoracic electrical bio impedance," Critical Care Medicine; 1986; vol. 14; pp. 904-909.

Thomas, et al.; "Bioimpedance spectrometer in the determination of body water compartments: Accuracy and clinical significance;" Appl. Radiation. Isotopes; vol. 49, No. 5/6; pp. 447-455; 1998.

Chetham, Scott; U.S. Appl. No. 12/090,078 entitled "Hydration status monitoring," filed Apr. 11, 2008.

McAdams et al.; Tissue impedance: a historical overview; Physiological Measurement, Institute of Physics Publishing, Bristol, GB; 16 (3A); pp. A1-A13; Aug. 1, 1995.

* cited by examiner

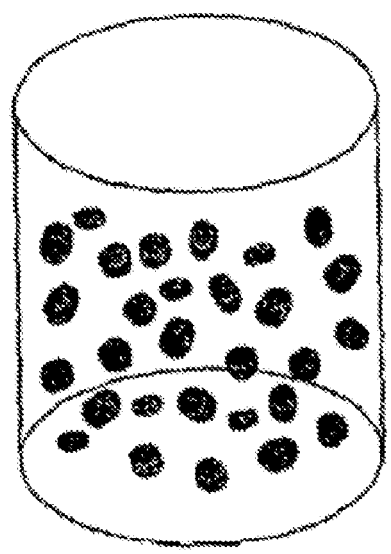 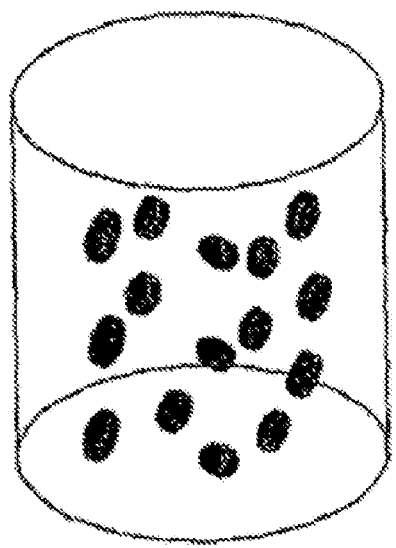 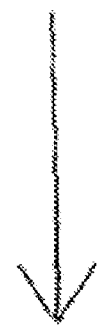
FIG. 3A  FIG. 3B
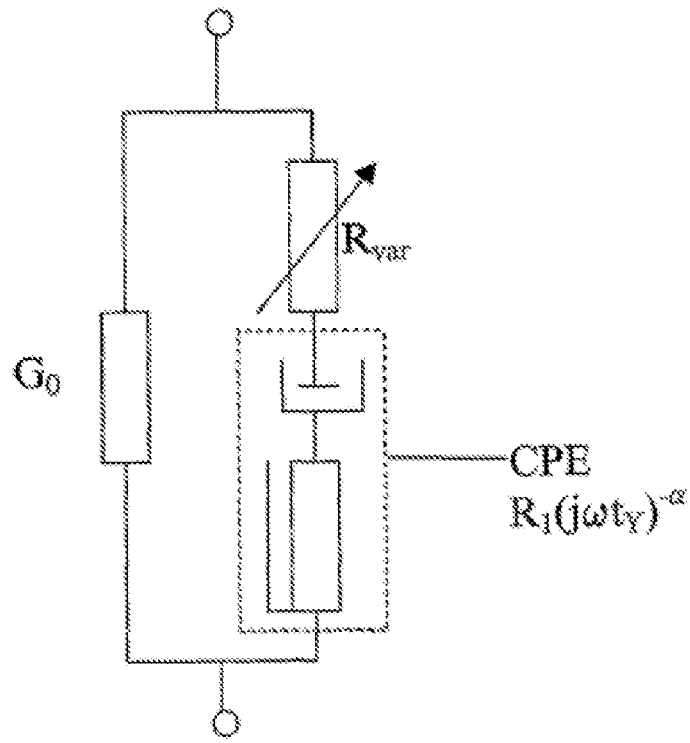
FIG. 4

CARDIAC MONITORING SYSTEM

CROSS REFERENCE TO RELATED APPLICATIONS

This application is the continuation in part of U.S. patent application Ser. No. 11/629,804, filed Dec. 15, 2006, now abandoned, which is a National Stage of International Application No. PCT/AU05/000893, filed Jun. 21, 2005, which application claims priority to Australian Application No. 2004903334, filed Jun. 21, 2004 and Australian Application No. 2004906181, filed Oct. 26, 2004, All of these applications are herein incorporated by reference in their entirety.

BACKGROUND OF THE INVENTION

The present invention relates to methods and apparatuses for monitoring biological parameters, and in particular to a method and apparatus for measuring cardiac function in a subject using bioelectric impedance or components of bioelectric impedance.

The reference to any prior art in this specification is not, and should not be taken as, an acknowledgment or any form of suggestion that the prior art forms part of the common general knowledge.

It is estimated that coronary heart disease will become the single biggest public health problem in the world by 2020, The treatment of coronary heart disease and other cardiovascular diseases therefore represents and increasingly large health and economic burden throughout the world in the coming years.

Cardiac output (CO), which can be defined as the amount of blood ejected by the ventricles of the heart per minute (measured in liters per minute), is governed by the metabolic demands of the body, and therefore reflect the status of the entire circulatory system. For this reason measurement of cardiac output is an essential aspect of haemodynamic monitoring of patients with heart disease or who are recovering from various forms of cardiovascular disease or other medical treatments.

One existing technique for determining cardiac function which has been developed is known as impedance cardiography (IC). Impedance cardiography involves measuring the electrical impedance of a subject's body using a series of electrodes placed on the skin surface. Changes in electrical impedance at the body's surface are used to determine changes in tissue volume that are associated with the cardiac cycle, and accordingly, measurements of cardiac output and other cardiac function.

A complication in impedance cardiography is that the baseline impedance of the thorax varies considerably between individuals, the quoted range for an adult is 20 Ω-48 Ω at a frequency between 50 kHz-100 kHz. The changes in impedance due to the cardiac cycle are a relatively small (0.5%) fraction of the baseline impedance, which leads to a very fragile signal with a low signal to noise ratio.

Accordingly, complex signal processing is required to ensure measurements can be interpreted.

An example of this is described in international patent publication no. WO2004/032738, In this example, the responsiveness of a patient to an applied current is modelled using the equivalent circuit shown in FIG. 1. The equivalent circuit assumes that:

direct current is conducted through the extracellular fluid only since the reactance of the cell membrane will be infinite;

an applied alternating current is conducted through the extracellular and intracellular pathways in a ratio dependent on the frequency of the applied signal.

Accordingly, the equivalent circuit includes an intracellular branch formed from a capacitance C representing the capacitance of the cell membranes in the intracellular pathway and the resistance $R_I$ representing the resistance of the intracellular fluid. The circuit also includes an extracellular branch formed from resistance $R_E$ which represents the conductive pathway through the tissue.

WO2004/032738 operates based on the assumption that the cardiac cycle will only have an impact on the volume of extracellular fluid in the patient's thorax, and therefore that cardiac function can be derived by considering changes in the extracellular component of the impedance. This is achieved by applying an alternating current at a number of different frequencies. The impedance is measured at each of these frequencies and then extrapolated to determine the impedance at zero applied frequency, which therefore corresponds to the resistance $R_E$. This is then determined to be solely due to the extracellular fluid component and hence can be used to determine attributes of cardiac function, such as stroke volume.

However, in practice the impedance at zero frequency would not be due solely to extracellular fluids but would be influenced by a number of other factors. In particular, cells do not act as a perfect capacitor and accordingly, the intracellular fluid will contribute to the impedance at a zero applied frequency.

A further issue in WO2004/032738 is that the process determines the impedance at zero applied frequency using the "Cole model". However, again this assumes idealised behaviour of the system, and consequently does not accurately model a subject's bioimpedance response. Consequently cardiac parameters determined using these techniques tend to be of only limited accuracy.

SUMMARY OF THE INVENTION

Described herein are methods and systems for determining one or more measures of cardiac function. In general, these methods may involve determining an actual characteristic frequency, measuring the instantaneous impedance or components of the impedance at that characteristic frequency, and using the instantaneous impedance (or a component of the impedance) value(s) to determine a measure of cardiac function. A characteristic frequency may be determined by analyzing the bioelectric response of the subject's body or tissue at various frequencies, as described in greater detail herein. An impedance (or a component of the impedance such as reactance, phase shift, magnitude, resistance) may be measured either directly or derived. A characteristic frequency may be determined for a particular subject either once, or periodically. For example, each measurement of instantaneous impedance may be made at a new characteristic frequency. This is described in greater detail below.

One variation of a method of determining a measure of cardiac function in a subject may include the steps of determining a characteristic frequency for the subject, determining the impedance or a component of the impedance at the characteristic frequency, and determining a measure of cardiac function using the impedance or a component of the impedance determined at the characteristic frequency.

In some variations, the characteristic frequency of the subject is determined by applying an electrical signal having a plurality of frequencies to the subject, determining an instantaneous impedance value at each of the plurality of frequencies, fitting the instantaneous impedance values to a frequency dependent function, and determining the characteristic frequency using the function. The characteristic frequency may be determined from an approximate maximum of the function. For example, the frequency dependent function may be a function based on a Wessel plot or a Cole plot, or a polynomial curve fit. The characteristic frequency may be determined over any appropriate frequency range. For example, the characteristic frequency may be determined by applying an electrical signal having a plurality of frequencies within the range of 2-10,000 kHz to the subject.

In some variations, the impedance (or a component of the impedance) at the characteristic frequency is determined by comparing an electrical signal applied to the subject (having a frequency at approximately the characteristic frequency) with an electrical signal received from the subject in response to the applied electrical signal. The component of impedance determined may be the reactance, the phase (e.g., phase shift) or the magnitude. For example, the reactance or the phase shift values measured at the characteristic frequency may be used to measure (or estimate) a characteristic cardiac function. In general, multiple ("instantaneous") values for the impedance or a component of the impedance may be determined during the course of a cardiac cycle.

Any appropriate measure of cardiac function may be determined using the characteristic frequency, including stroke volume and cardiac output. For example, stroke volume may be determined by multiplying the maximum change in impedance during a cardiac cycle by one or more constants including constants based on the subject's physical characteristics. As mentioned, the measure of cardiac function may be determined using the impedance (or a component of the impedance) at the characteristic frequency for a number of sequential time points. For example, instantaneous reactance values may be taken during an entire (or a portion of a) cardiac cycle. The same characteristic frequency may be used to determine the instantaneous impedance values used to determine the measure of cardiac function, or the characteristic frequency may be repeatedly determined for each time point or a subset of time points. For example, the measure of cardiac function may be determined by determining the characteristic frequency and the instantaneous reactance at the characteristic frequency for a number of sequential time points.

Also described herein are methods of determining a measure of cardiac output in a subject including the steps of applying an electrical signal having a plurality of frequencies to the subject, receiving an electrical signal from the subject in response to the applied signal, determining a characteristic frequency for the subject by comparing the applied and received electrical signals, determining at least one component of the impedance at the characteristic frequency, and determining a measure of cardiac function using the at least one component of the impedance determined at the characteristic frequency. As mentioned, the characteristic frequency may be determined by comparing the applied and received electrical signals to determine an instantaneous impedance value and fitting the instantaneous impedance values to a frequency dependent function. The at least one component of the impedance determined at the characteristic frequency may be the reactance, the phase (e.g., phase shift), the magnitude, or the resistance.

Any appropriate measure of cardiac function may be determined, including stroke volume and/or cardiac output. For example, indicia of cardiac function may be determined by first identifying the characteristic frequency, and then determining the instantaneous reactance values at the characteristic frequency for a number of sequential time points (e.g., during a full cardiac cycle). A measure of cardiac function may be determined by determining the instantaneous phase shift values at the characteristic frequency for a number of sequential time points during a cardiac cycle. As mentioned above, the measure of cardiac function may be determined by determining the characteristic frequency and at least one component of the impedance at the characteristic frequency for a number of sequential time points during a cardiac cycle.

Also described herein are systems for analyzing cardiac function in a subject. These systems may include a plurality of electrodes configured to be attached to a subject, and a processor connected to the plurality of electrodes. The processor may be configured to control the application of an electrical signal having a plurality of frequencies to the subject, receive an electrical signal from the subject in response to the applied signal, determine a characteristic frequency by comparing the applied and received electrical signals, determine at least one component of the impedance at the characteristic frequency, and determine a measure of cardiac function using the at least one component of the impedance determined at the characteristic frequency. In some variations, the system also includes a signal generator coupled to processor for generating the electrical signals applied to the subject. The systems may also include one or more sensors for detecting the electrical signals from the subject in response to the applied electrical signals.

In some variations, the system may also include processing logic for determining the measure of cardiac output by multiplying the at least one component of the impedance (e.g., reactance, phase shift) by one or more constants including constants based on the subject's physical characteristics. The processing logic may be implemented by software, hardware, or any combination of these. Thus, the processor may be a microprocessor configured to execute the processing logic.

Any of the systems described herein may also include one or more input devices in communication with the processor for entering at least some of the subject's physical characteristics. For example, the systems may include a keypad, mouse, memory, wireless connection or the like for receiving input. Physical characteristics may include height, gender, weight, pulse rate, age, ethnicity, etc.

BRIEF DESCRIPTION OF THE DRAWINGS

FIGS. 3A and 3B are schematics of an example of the effects of blood flow on blood cell orientation.

FIG. 4 is a schematic of a second example of an equivalent circuit used to model the conduction characteristics of biological tissue.

DETAILED DESCRIPTION OF THE INVENTION

Figure 2:
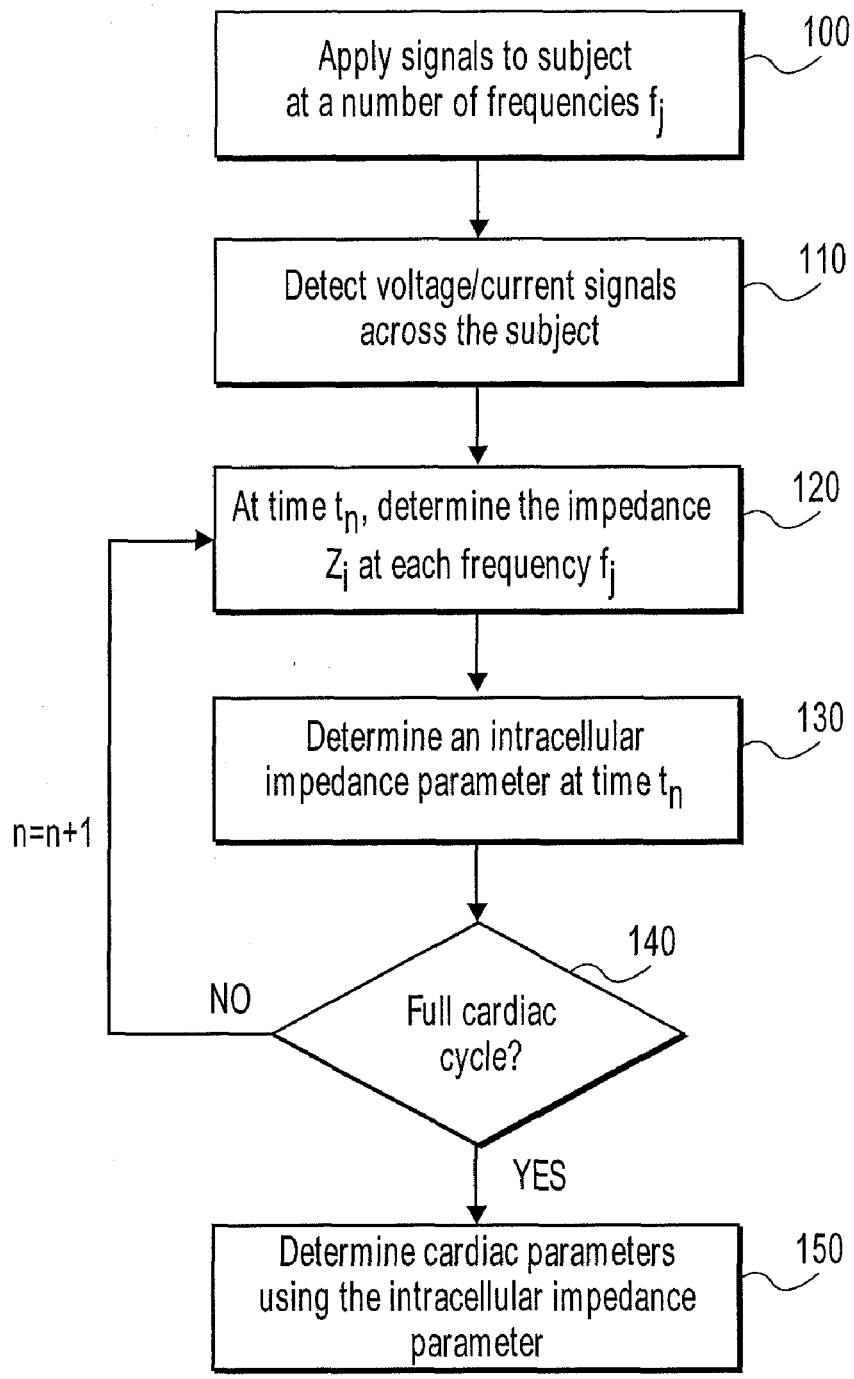
FIG. 2 is a flowchart of an example of a process for determining cardiac function.

An example of a process for determining parameters of cardiac function relating to a subject is described with reference to FIG. 2.

In particular at step 100, alternating electrical signals are applied to the subject at a number of different frequencies $f_i$, with electrical signals across the subject being detected at each of the respective $f_i$, at step 110. The nature of the signals applied and detected will depend on the implementation as will be described below.

At step 120, at a first time instance $t_n$, the impedance $Z_i$ at each frequency $f_i$ is determined. At step 130, the impedance is used to determine an intracellular impedance parameter at the time $t_n$. In one example, this is achieved utilising an appropriate model, such as a CPE (constant phase element) model, which will be described in more detail below.

This is performed for a number of sequential time instance $t_n, t_{n+1}, t_{n+2}$ until it is determined that a complete cardiac cycle has been analyzed at step 140. This may be achieved by monitoring appropriate ECG signals, or alternatively simply by processing sufficient time instances to ensure that a cardiac cycle has been detected.

At step 150, the intracellular impedance parameter, and in one example, changes in the intracellular impedance parameter, is used to determine cardiac parameters.

This technique takes into account that the impedance fluctuation of the thorax during the cardiac cycle is dependent on both changes in blood volume and changes in the impedance in the blood itself.

Blood is a suspension of erythrocytes, with a high resistivity, and other cells in a conducting fluid called plasma. The erythrocytes of stationary blood are randomly oriented as shown in FIG. 3A, and hence the resistivity of stationary blood is isotropic. Due to their biconcave shape erythrocytes tend to align themselves in flowing blood with their axes parallel to the direction of flow as shown in FIG. 3B. Accordingly, the resistivity of flowing blood is anisotropic.

The anisotropy of the resistivity is due to the longer effective path length for the current travelling normal to the axis of the vessel compared with the current flowing parallel to the vessel. As a result, the resistance of the intracellular fluid alters depending on the orientation of the erythrocytes, and hence depends on the flow of blood.

Furthermore, the extent of the anisotropy is shear-rate dependent since the orientation of the erythrocytes is influenced by the viscous forces in flowing blood. As a result, the resistivity is in turn also dependent on the flow rate.

Figure 1:
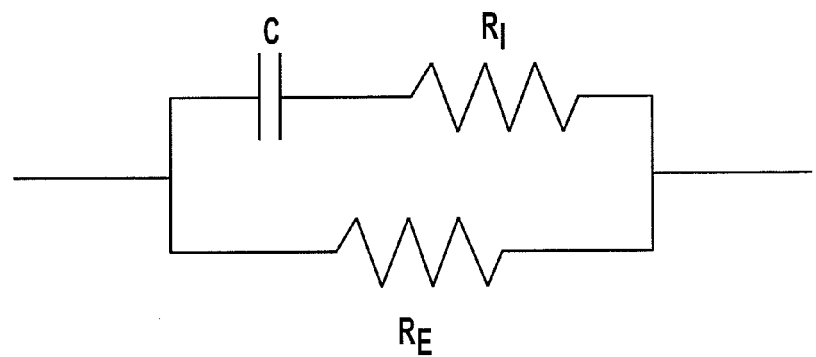
FIG. 1 is a schematic of an example of an equivalent circuit used to model the conduction characteristics of biological tissue.

It is therefore possible to take this into account by determining cardiac function on the basis of intracellular parameters, as opposed to using extracellular impedance parameters as in the prior art. This can therefore be achieved using the equivalent circuit shown in FIG. 1, and by using the impedance measurements to determine the impedance parameters based on the capacitance C and the resistance $R_1$ of the intracellular branch.

Thus, in this instance, the impedance measurements can be used to determine values for the intracellular resistance $R_T$ and the capacitance C, for example, by determining values of $R_0$ and $R_\infty$, and then using these to solve the Cole equation using appropriate mathematical techniques.

In this instance however, modelling the resistivity as a constant value does not accurately reflect the impedance response of a subject, and in particular does not accurately model the change in orientation of the erythrocytes, or other relaxation effects.

To more successfully model the electrical conductivity of blood, an improved CPE based model can be used as will now be described with respect to FIG. 4.

In this example, to accurately determine the characteristic impedance, and interpret the contribution of cardiac effects to the impedance, an equivalent circuit based on a free conductance parallel model is used, as shown in FIG. 4. Such a model can also be created in a series form and the parallel model is shown here for illustration.

In this example, the circuit includes an extracellular conductance $G_0$ that represents the conductance of electrical current through the extracellular fluid. The intracellular conduction path includes a constant phase element (CPE) represented as the series connection of a frequency dependent conductance, and a frequency dependent capacitance.

The two equations below define a general CPE:

$$Y_{CPE} = (\omega\tau)^m (G_{m\tau=1} + jB_{\omega\tau=1}) \quad (1)$$

$$\varphi_{cpe} = \frac{\arctan B}{G} \quad (2)$$

where:
$Y_{CPE}$ is the admittance of the CPE and
$\phi_{cpe}$ is the phase of the CPE.

In this equation $\tau$ represents a frequency scale factor and, $\omega\tau$ is dimensionless.

The parameter m defines the extent of the frequency dependence of the admittance of the CPE $Y_{CPE}$ and the frequency scale factor with $\tau$. It is known that for biological tissue m is in the range of $0 \leq m \leq 1$.

In one example, the CPE is in accordance with Fricke's law ($CPE_F$) although other forms of CPE could be used. It is usual practice to use the exponent symbol $\alpha$ (m=$\alpha$) for Fricke CPE's.

In order to make the model compatible with relaxation theory, the series ideal resistor is changed to a free resistor parameter $R_{var}$ so that the characteristic time constant $\tau_r$ will be a dependent parameter.

The result is that the conductance of the circuit can be expressed as follows:

$$Y = G_0 + \frac{1}{R_{var} + R_1(j\omega\tau_z)^{-\alpha}} \quad (3)$$

$$\tau_{Ym} = \frac{1}{\omega_{Ym}} = \tau_Y \left(\frac{R_1}{R_{var}}\right)^{\frac{1}{-\alpha}} \quad (4)$$

Here $\tau_{Ym}$ is a new characteristic time constant. The subscript m is used to identify the new variable from the previous variables and is consistent with the nomenclature know to those skilled in the art.

By putting a nominal fixed value to the time constant $\tau_y$, it is possible to follow the CPE by calculating the $R_1$ using the equation.

$$R_1 = \frac{R_{var}}{(\tau_Y \omega_{Ym})^{-\alpha}} \quad (5)$$

In this instance, the variable resistance parameter $R_{var}$ is dependent on the orientation of the erythrocytes and as a result, changes in $R_{var}$ can be used to determine the rate of flow of blood within a subject. Consequently, it is possible to determine information regarding cardiac output, or the like.

Figure 5:
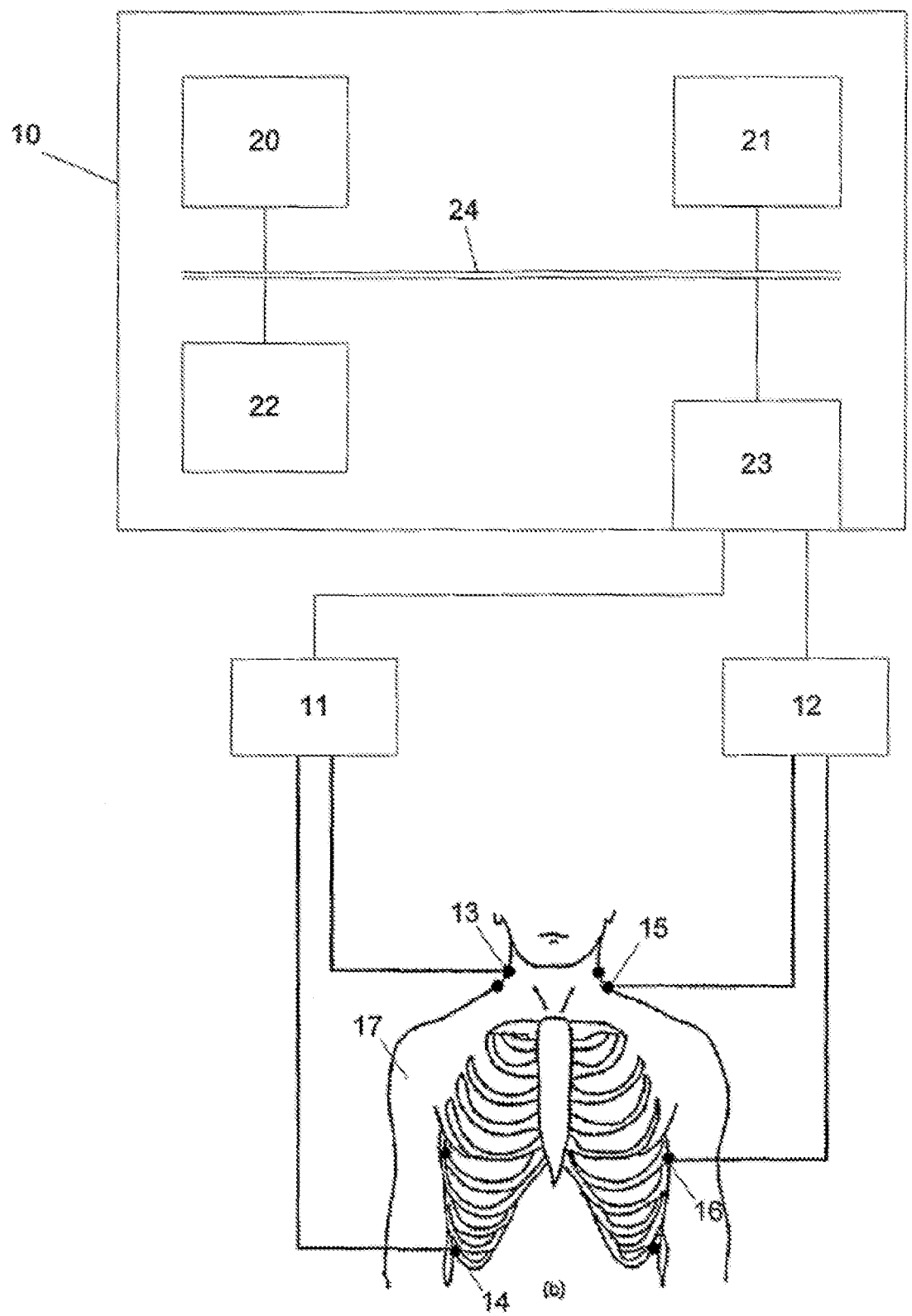
FIG. 5 is a schematic of an example of apparatus for determining cardiac function.

An example of apparatus suitable for performing an analysis of a subject's bioelectric impedance to determine cardiac function will now be described with reference to FIG. 5.

As shown the apparatus includes a processing system 10 having a processor 20, a memory 21, an input/output (I/O) device 22 and an interface 23 coupled together via a bus 24. The processing system is coupled to a signal generator 11 and a sensor 12 as shown. In use the signal generator 11 and the sensor 12 are coupled to respective electrodes 13, 14, 15, 16, as shown.

In use, the processing system 10 is adapted to generate control signals, which causes the signal generator 11 to generate an alternating signal which is applied to a subject 17, via the electrodes 13, 14. The sensor 12 then determines the voltage or current across the subject 17 and transfers appropriate signals to the processing system 10.

Accordingly, it will be appreciated that the processing system 10 may be any form of processing system which is suitable for generating appropriate control signals and interpreting voltage data to thereby determine the subject's bioelectrical impedance, and optionally determine the cardiac parameters.

The processing system 10 may therefore be a suitably programmed computer system, such as a laptop, desktop, PDA, smart phone or the like. Alternatively the processing system 10 may be formed from a specialised hardware. Similarly, the I/O device may be of any suitable form such as a touch screen, a keypad and display, or the like.

It will be appreciated that the processing system 10, the signal generator 11 and the sensor 12 may be integrated into a common housing and therefore form an integrated device. Alternatively, the processing system 10 may be connected to the signal generator 11 and the sensor 12 via wired or wireless connections. This allows the processing system 10 to be provided remotely to the signal generator 11 and the sensor 12. Thus, the signal generator 11 and the sensor 12 may be provided in a unit near, or worn by the subject 17, whilst the processing system is situated remotely to the subject 17.

In practice, the outer pair of electrodes 13, 14 are placed on the thoracic and neck region of the subject and an alternating signal is applied at a plurality of frequencies either simultaneously or in sequence, (two are sufficient but at least three are preferred with five or more being particularly advantageous) in the range 2-10,000 kHz. However the applied waveform may contain more frequency components outside of this range.

In the preferred implementation the applied signal is a frequency rich voltage from a voltage source clamped so it does not exceed the maximum allowable patient auxiliary current. The signal can either be constant current, impulse function or a constant voltage signal where the current is measured so it does not exceed the maximum allowable patient auxiliary current.

A potential difference and/or current are measured between an inner pair of electrodes 16, 17. The acquired signal and the measured signal will be the superposition of signals at each of the applied frequencies and the potentials generated by the human body, such as the ECG.

Optionally the distance between the inner pair of electrodes may be measured and recorded. Similarly, other parameters relating to the subject may be recorded, such as the height, weight, age, sex, health status, and other information, such as current medication, may also be recorded.

The acquired signal is demodulated to obtain the impedance of the system at the applied frequencies. One suitable method for demodulation is to use a Fast Fourier Transform (FFT) algorithm to transform the time domain data to the frequency domain. Another technique not requiring windowing of the measured signal is a sliding window FFT. Other suitable digital and analog demodulation techniques will be known to persons skilled in the field.

Impedance or admittance measurements are determined from the signals at each frequency by comparing the recorded voltage and current signal. The demodulation algorithm will produce an amplitude and phase signal at each frequency.

Figure 6A:
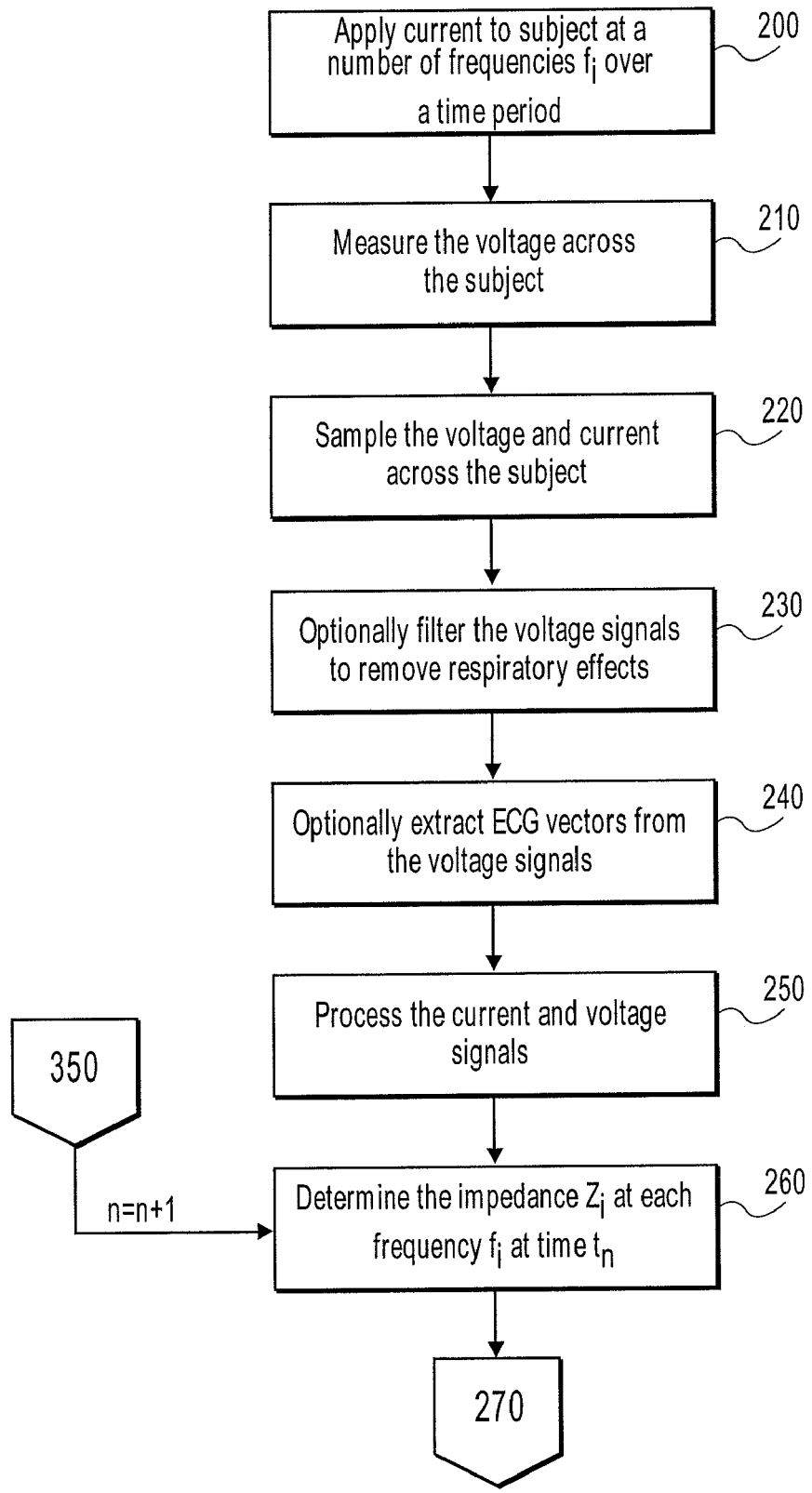
FIGS. 6A to 6C are a flowchart of a second example of a process for determining cardiac function.
Figure 6B:
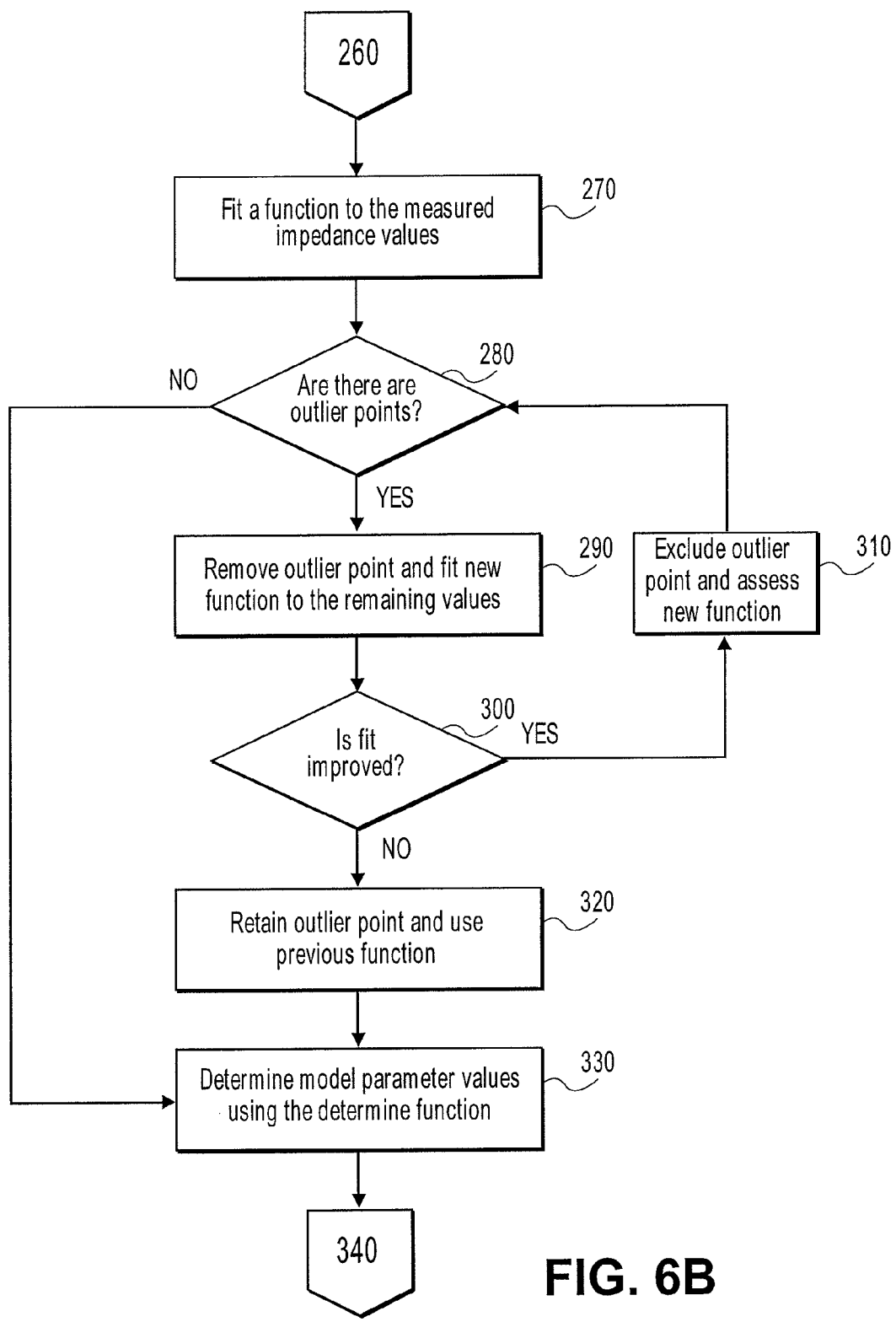

An example of the process of measuring a subject's bioelectric impedance and then interpreting this will be described in more detail with reference to FIGS. 6A to 6C.

At step 200 the processing system 10 generates predetermined control signals causing the signal generator 11 to apply current signals to the subject 17 at a number of frequencies $f_i$, over a time period T. The current signals applied to the subject 17 may be provided at the frequencies $f_i$ sequentially, or simultaneously, by superposing a number of signals at each corresponding frequency $f_i$.

It will be appreciated that the control signals are typically generated in accordance with data stored in the memory 21 and this can allow a number of different current sequences to be used, with selection being made via the I/O device 22, or via another appropriate mechanism.

At step 210 the sensor 12 measures the voltage across the subject 17. In this regard, the voltage signals will typically be analogue signals and the sensor 12 will operate to digitise these, using an analogue to digital converter (not shown).

At step 220 the processing system 10 samples the signals from the signal generator 11 and the sensor 12, to thereby determine the current and voltage across the subject 17.

At step 230, a filter is optionally applied to the voltage signals at step 230 to remove respiratory effects, which typically have a very low frequency component in line with the patient's rate of breathing. It will be appreciated that filtering may be achieved by the sensor 12 or the processing system 10, depending on the implementation.

At step 240 ECG vectors are optionally extracted from the voltage signals. This can be achieved as the ECG signals typically have a frequency in the region 0 Hz to 100 Hz, whereas the impedance signals are in the region of 5 kHz to 1 MHz. Accordingly, the ECG signals may be extracted by any suitable technique, such as demodulation, filtering or the like.

At step 250 the signals may also undergo additional processing. This can be performed, for example, by further filtering the signals to ensure that only signals at the applied frequencies $f_i$, are used in impedance determination. This helps reduce the effects of noise, as well as reducing the amount of processing required.

At step 260, the current and voltage signals sampled at time $t_n$ to determine the impedance $Z_i$ at each frequency $f_i$.

At step 270 a function is fitted to the impedance values.

Figure 7:
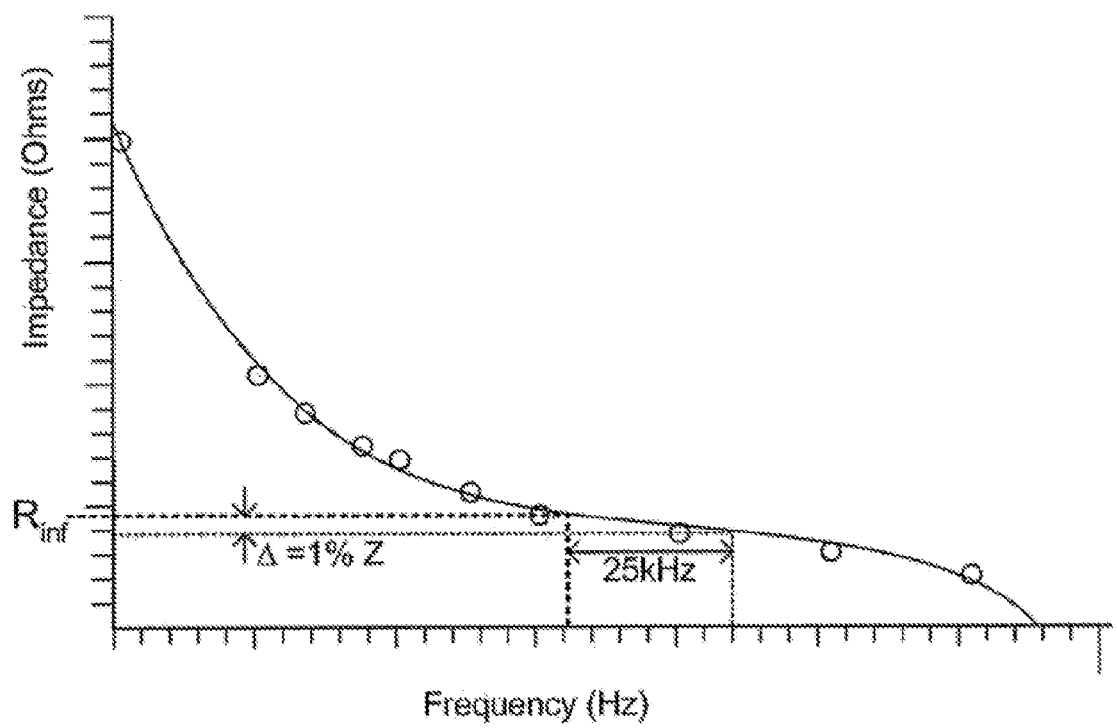
FIG. 7 is an example of a graph of impedance plotted against frequency for an impedance measurement.

An example of this is shown in FIG. 7, which shows an example of the appearance of the impedance data and function when plotted against frequency. It will be appreciated that the plot is for the purpose of example only, and in practice the processing system 10 will not necessarily generate a plot. In the case of the frequency versus the impedance plot shown in FIG. 7, the function is typically a polynomial and in particular in this example is a sixth order polynomial.

Figure 8:
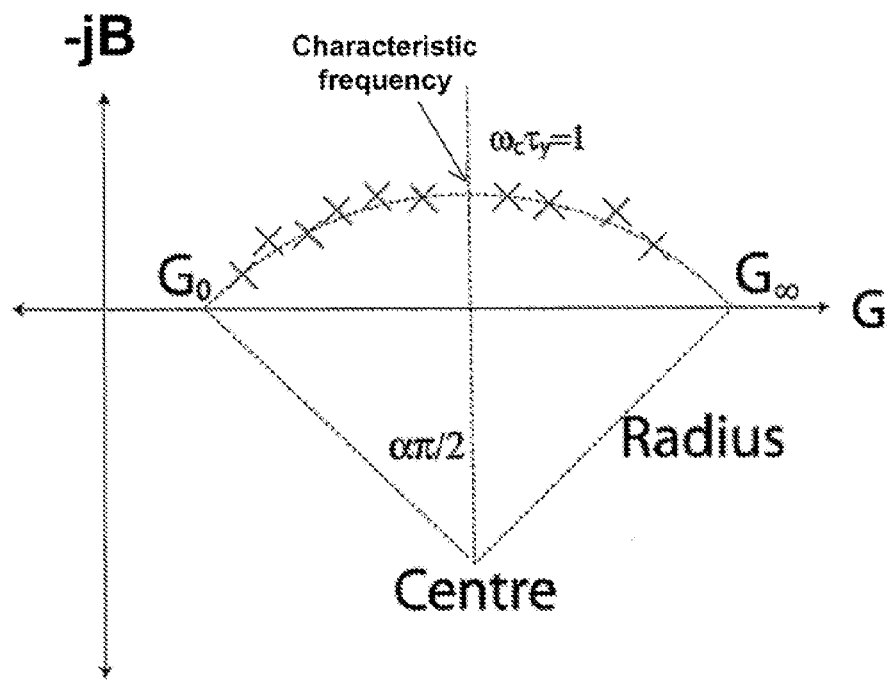
FIG. 8 is an example of a Wessel diagram of susceptance plotted against conductance.

Alternatively a Wessel plot may be used as shown in FIG. 8, as will be described in more detail below.

In practice noise elimination may be necessary to accurately fit a function to the data. In one example, elimination of noise at certain frequencies can be performed by initially fitting a function to the measured data and then systematically removing outlier points from the data set and re-fitting the function to the reduced data set.

Accordingly, at step 280 the processing system 10 operates to determine if there are outlier points, which are considered to be points that are greater than a predetermined distance from the determined function.

It will be appreciated that the function used, and the determination of outlier points may be achieved utilising standard mathematical techniques.

If it is determined that there are outlier points, these are removed from the data set and a new function fitted to the remaining values at step 290. At step 290 the processing system 10 determines if the fit is improved and if so the outlier point is excluded from the data set permanently with the new function being assessed at step 310. This is repeated until all outliers that affect the data are removed.

If it is determined that the fit is not improved at step 300 the outlier is retained and the previous function used at step 320.

If there are no outliers, or once outliers have been excluded from the data set, the plot is then used to determine values from $R_o$ and $R_\infty$ using the determined function.

In one example, the function is used to calculate $R_0$ and $R_\infty$. Alternatively, this can be used to determine the impedance at the characteristic frequency. As is apparent to one of skill in the art, the characteristic frequency is apparent from this procedure (e.g., the maximum reactance in the frequency range).

For example, in the case of the function shown in FIG. 7, $R_\infty$ can be determined by finding the impedance at the start of the pseudo-plateau, i.e. a relatively flat portion, on the curve of FIG. 7. In the illustrative embodiment the pseudo plateau is identified using a rule-based approach.

In this approach the function is analysed to find the frequency where impedance (Z) changes ($\Delta Z$) by less than 1% with a frequency increase of 25 kHz. The resistance or impedance Z measured at this frequency is identified as $R_\infty$ and represents resistance of the circuit if an infinitely high frequency was applied. Other methods of determining this pseudo-plateau region may be known to those skilled in the art.

Similarly, the impedance at zero applied frequency $R_0$ can be determined as the value at which the function would intercept the y-axis.

If a "Wessel" plot type function is used, as shown in FIG. 8, this approach uses an arc, which allows the characteristic impedance to be determined. In this example, the apex of the arc in the complex Wessel plane no longer corresponds to the nominal value of $\tau_Y$, but to $\tau_{Ym}$ as given by the above equation. In some variations, the characteristic frequency (the frequency at the character impedance) may be determined by solving a Cole-Cole model for the peak. Thus, the characteristic frequency may be determined directly (e.g., by extrapolating from a curve fitting), or it may be numerically determined. J. Xiang et al., ("On the Adequacy of Identified Cole-Cole Models," Computers & Geosciences 29 (2003); 647-654) describes methods of numerically determining a Cole-Cole model that may be used to determine the characteristic frequency.

Additionally $\alpha$ can be determined from the angle subtended by the arcuate locus from $R_0$ to $R_\infty$. By comparing this to m determined from susceptance data, this allows whether the Fricke criteria for relaxation phenomena of biological materials is met. In the event that they are equal or within a predetermined range of each other, then the Wessel diagram method may be applied with reasonable accuracy. In the event that m and $\alpha$ are not sufficiently close in value then the function fitting approach described above is a more appropriate method for determining the quantities of interest for the free conductance model.

At step 340 the processing system 10 uses the values of either $R_0$ to $R_\infty$, or the characteristic impedance, together with equation (5) to determine the intracellular impedance parameter, which in this example is the intracellular variable resistance parameter $R_{var}$.

As an alternative to determining values of $R_0$, $R_\infty$, or the characteristic impedance $Z_o$, the equation (5) can alternatively be solved mathematically, for example by using a number of different impedance values at different frequencies $f_i$ to solve a number of simultaneous equations. These values can be based on directly measured values, although preferably these are values determined from the fitted function, to thereby take into account the impedance response across the range of applied frequencies $f_i$.

At step 350 it is determined if a full cardiac cycle has been completed and if not the process returns to step 240 to analyse the next time instance $t_{n+1}$.

At step 360, once a full cardiac cycle has been completed, the processing system 10 operates to determine the change in the intracellular resistance parameter $R_{var}$ over the cardiac cycle before using this to determine cardiac parameters at step 370.

Figure 9:
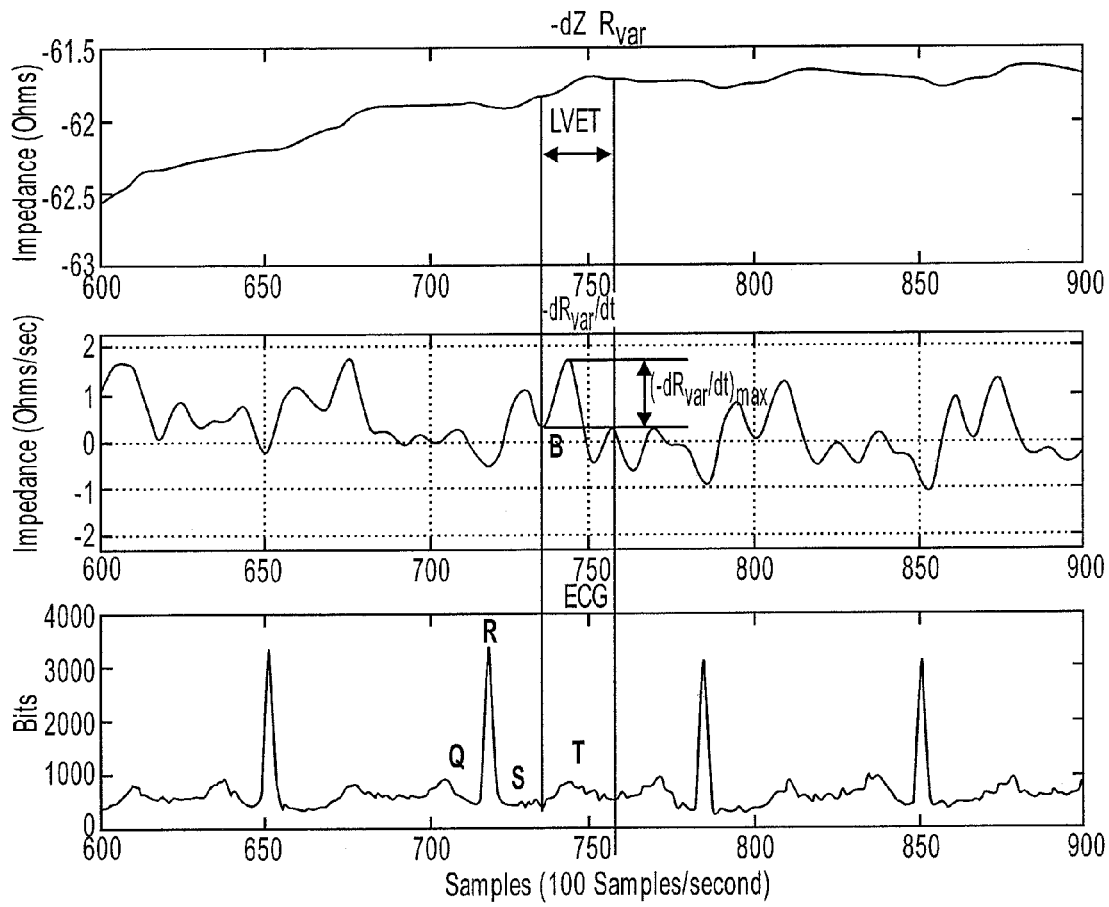
FIG. 9 is an example of three plots depicting the time varying impedance of the thorax, the level of impedance change due to cardiac function and an ECG.

A typical plot of the time varying impedance obtained by the present method is shown in FIG. 9.

In FIG. 9 the raw impedance data is plotted against time (measured by sample number) in the top graph. This graph includes the impedance from all time varying impedance components in the thoracic cavity including variation in blood volume, blood cell orientation and changes due to respiration.

The centre graph of FIG. 9 depicts the rate of change of impedance attributable to cardiac function of a patient. The graph was generated by removing the low frequency components from the top graph and obtaining the rate of change of impedance from the remaining data.

As will be appreciated by those skilled in the art additional measurements can also be incorporated into the present method or conducted simultaneously. For example, the inner electrodes can also be used to record ECG vectors. In order to generate more ECG vectors more inner electrode combinations are required. The outer electrodes can also be used to record the ECG vectors. The processing unit, or the operator, can automatically or manually select the most appropriate ECG vector. An external ECG monitor can also be connected or alternatively a separate module can be incorporated into the invention with additional electrodes to calculate the ECG vectors.

The ECG can advantageously be used to aid in the determination of cardiac events. An example ECG output is depicted in the lower graph of FIG. 9.

To calculate certain cardiac parameters from the impedance waveform, fiducial points must also be suitably identified. The ECG data and/or other suitable physiological measurement techniques may be employed to aid this process.

Other physiological parameters that could be used to assist in identifying fiducial points in the cardiac cycle include invasive/non-invasive blood pressure, pulse oximetry, peripheral bioimpedance measurements, ultrasound techniques and infrared/radio frequency spectroscopy. Such techniques can be used singularly or in a plurality to optimally determine cardiac event timing.

In one example an artificial neural network or weighted averages to determine the cardiac events as identified by conductance measurements combined with other methods of physiological measures offer an improved method of identifying these points. In the present example the start and end of left ventricular ejection are indicated by the vertical lines on the graphs of FIG. 9. The time between these points is the left ventricle ejection time (LVET).

These fiducial points can be used to obtain impedance values of interest. For example, the maximum rate of change in the intracellular resistance value $R_{var}$ over left ventricle ejection which is indicated on the central graph of FIG. 9 as:

$$\left(\frac{dR_{var}(t)}{dt}\right)_{MAX}$$

Measures of cardiac function can then be determined from this data. For example, the following method can be used to calculate blood velocity and stroke volume. The present example uses impedance measures to calculate cardiac output. However the same functions can be described using admittance or a combination of the two. The following formula can be used to calculate cardiac output:

$$CO = k_1 c_1 \left(\frac{\left|\left(\frac{dR_{var}(t)}{dt}\right)_{MAX}\right|}{Z_0}\right)^n * \left(\frac{1}{T_{RR}}\right)^m \times T_{LVE}$$

Where:
CO denotes cardiac output (liters/min), $$\left(\frac{dR_{var}(t)}{dt}\right)_{max}$$

is as indicated on FIG. 9;
$k_1$ is an optional population specific correction factor based on one or more subject parameters, such as at least the height and weight, but can also include distance between the electrodes and age;
$c_1$ is an optional calibration coefficient used to convert the units from Ohmic units to liters (which may be uniquely defined at manufacture for each monitoring device used to implement the method),
$Z_0$ is an optional baseline Impedance measured at the characteristic frequency (between 10 Ohms and 150 Ohms),
$T_{RR}$ is the interval between two R waves obtained from the ECG (found from the ECG or impedance or conductance data),
$T_{LVE}$ is left ventricular ejection time (measured from either the conductance or impedance curve or preferably a combination of other physiological measurement techniques) and
n (range . . . 4>n<4) and m (range . . . 4>m<4) are optional constants.

The person skilled in the art will be able to determine appropriate values for these constants dependent upon the patient and situation in which the method is applied.

Whilst the example described above has been described in the context of providing determining cardiac output of the heart, embodiments of the present invention can be applied to determine other measures of cardiac performance, including but not limited to, stroke volume, cardiac index, stroke index, systemic vascular resistance/index, acceleration, acceleration index, velocity, velocity index, thoracic fluid content, left ventricular ejection time, Pre-ejection period, systolic time ratio, left cardiac work/index, heart rate and mean arterial pressure.

As described briefly above, measures of cardiac performance and function may also be determined using the characteristic frequency. Thus, the characteristic frequency may be determined during a cardiac cycle by applying an electrical signal having a plurality of frequencies (or multiple electrical signals at different frequencies), detecting electrical signals in response to the applied signals, processing the detected signals (e.g., to remove unwanted components such as ECGs and other signals), comparing the applied electrical signals at each frequency with the response signals at each frequency, and fitting the signals to a function from which the characteristic frequency may be determined. As previously described, FIGS. 6A and 6B illustrate this. In this example, instantaneous impedance values are determined for each frequency $f_i$ at time $t_o$ 260, and are fit to a function 270 (such as the Wessel plot shown in FIG. 8). The characteristic frequency may be identified from the function. For example, the characteristic frequency from the Wessel plot is the frequency at the top of the arch (e.g., the frequency with the largest reactance). In practice, the characteristic frequency may be determined by approximating the maximum reactance over the applied frequency range.

The signal(s) applied to the subject may be a signal (or signals) having a plurality of frequency components, or a series of signals at different frequencies. The response signal that is measured from the subject after the application of one or more electrical signals arises because of the electrical properties of the body. This response is usually referred to as a response signal. The response signal may also be referred to as an evoked response or evoked signal, and is typically a passive response. For example, the response does not usually include a regenerative evoked (e.g., active) response from electrically active tissue.

Once the characteristic frequency has been determined, this characteristic frequency may provide a relatively accurate means of determining cardiac function by then applying an electrical signal at the characteristic frequency and receiving the response electrical signal at that frequency. This electrical stimulation and sampling may be repeated during a complete or partial cardiac cycle. For each time point, the stimulated and response signals may be compared (e.g., after filtering or other signal processing) to determine an instantaneous impedance or any components of the instantaneous impedance, such as resistance, reactance, phase and magnitude. As is known in the art, the resistance and reactance, and the impedance and phase are all mathematically related, and with any two you can calculate the other two. Further, as is known in the art, any of these components can be determined from the applied and response signals.

Figure 6C:
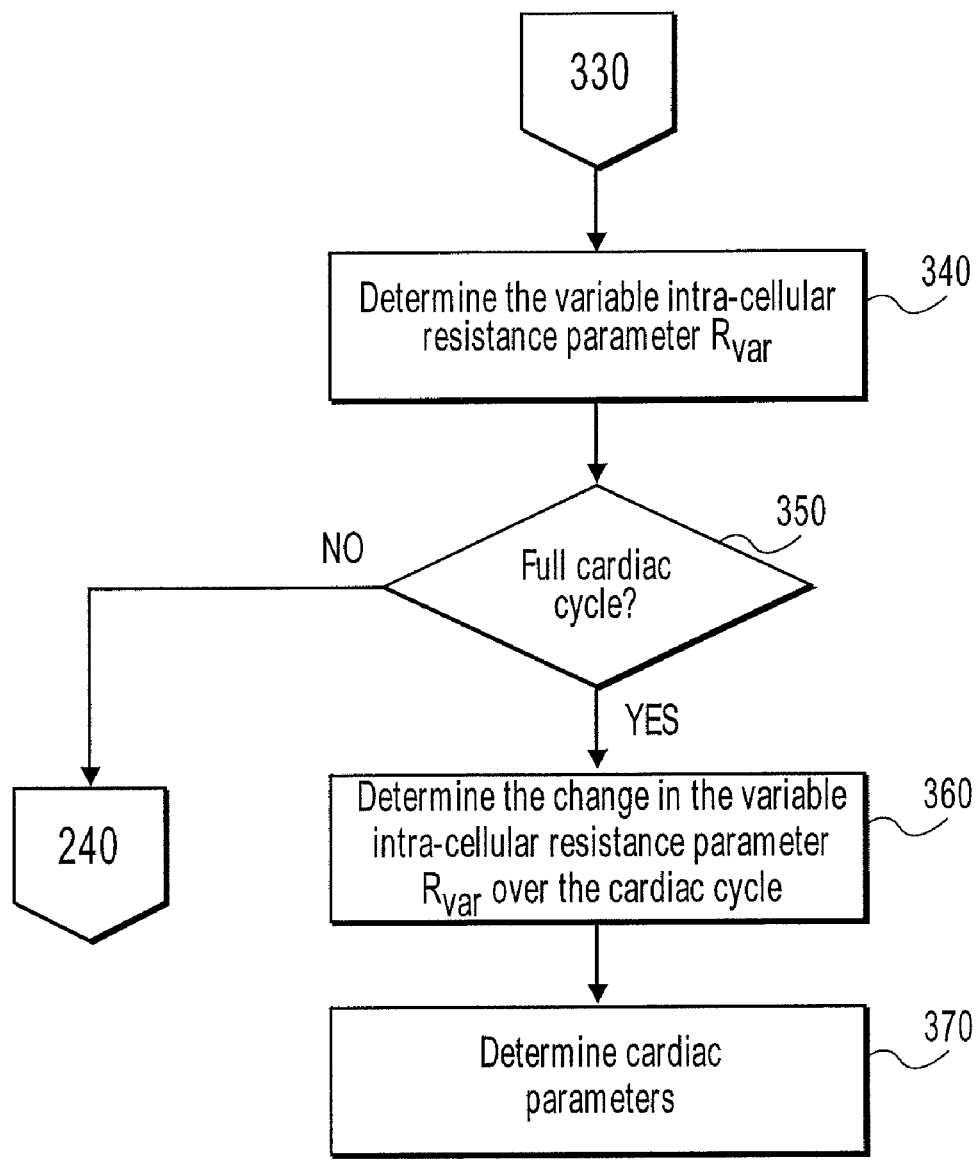
Figure 10:
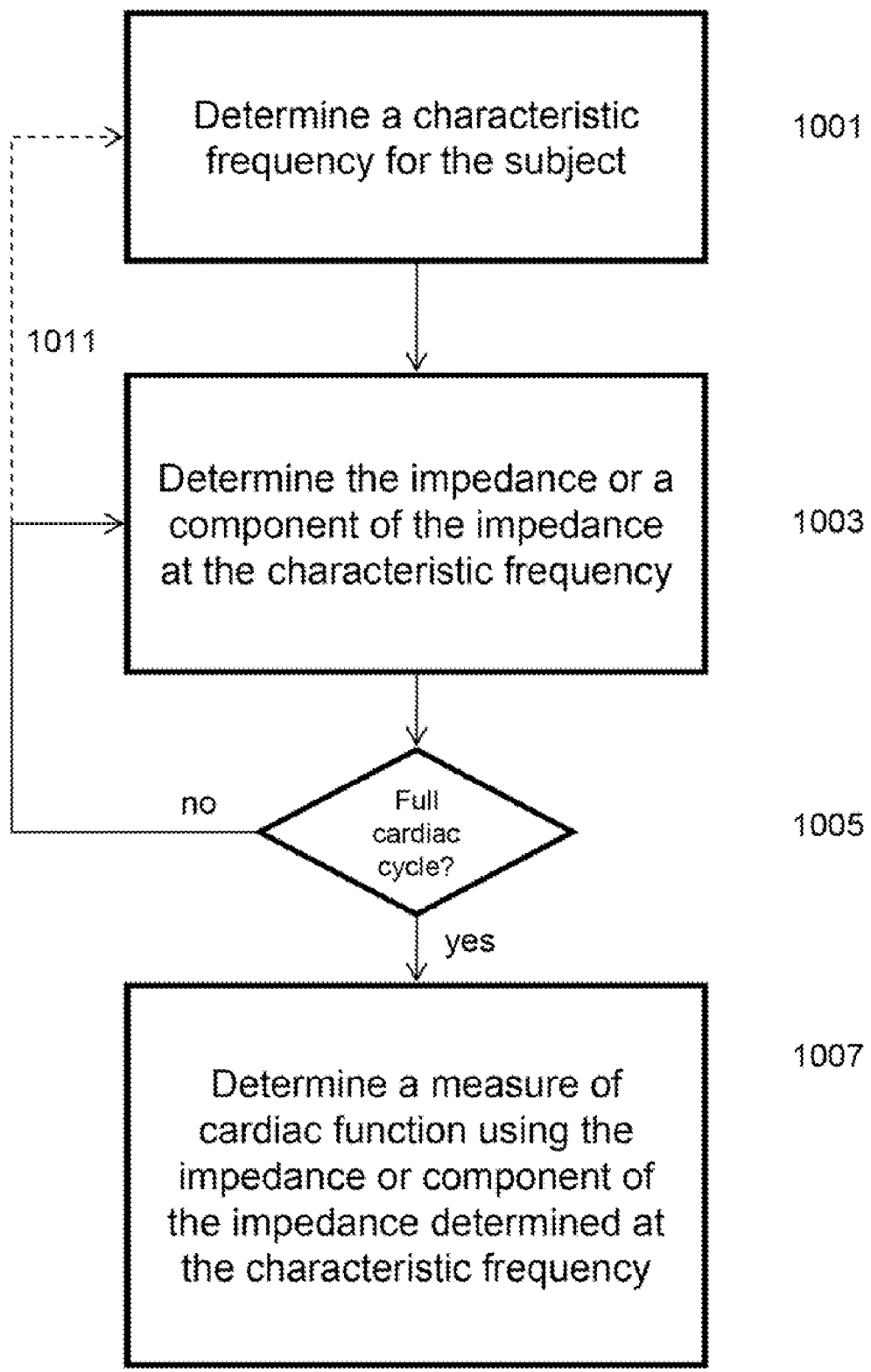
FIG. 10 is an exemplary flowchart of an example of a process for determining cardiac function.
Figure 11:
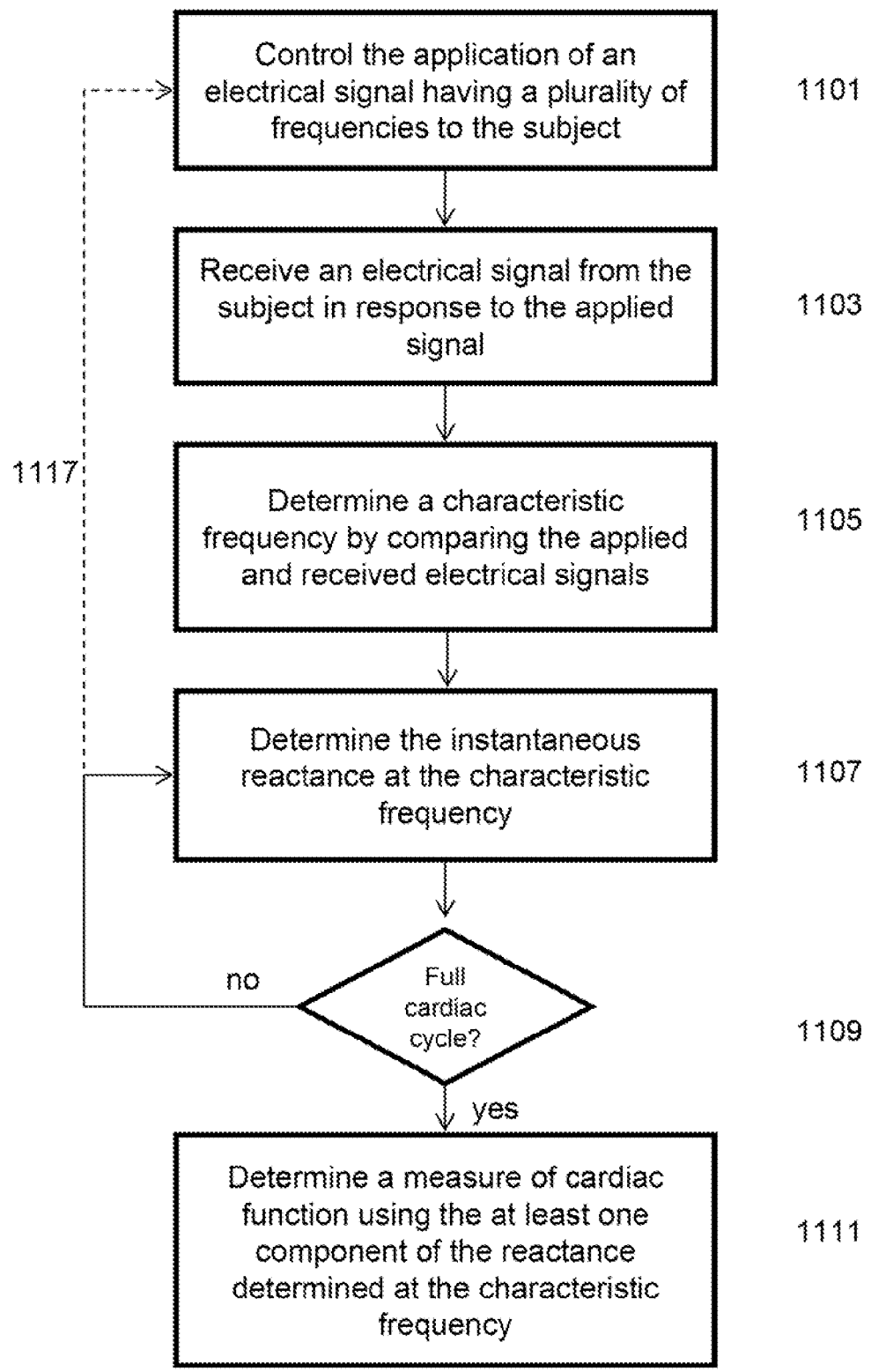
FIG. 11 is another exemplary flowchart of an example of a process for determining cardiac function.
Figure 5:
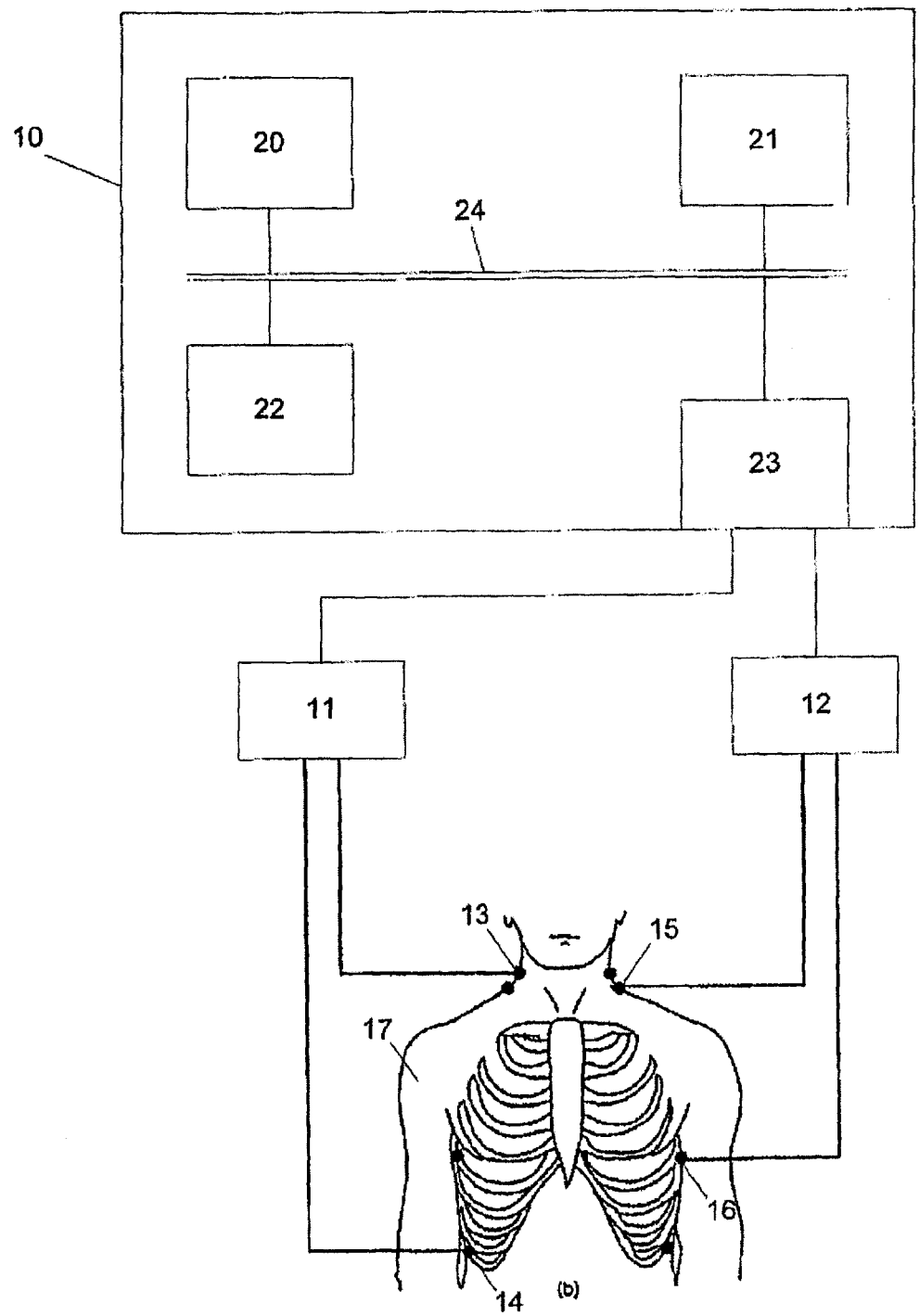
Figure 7:
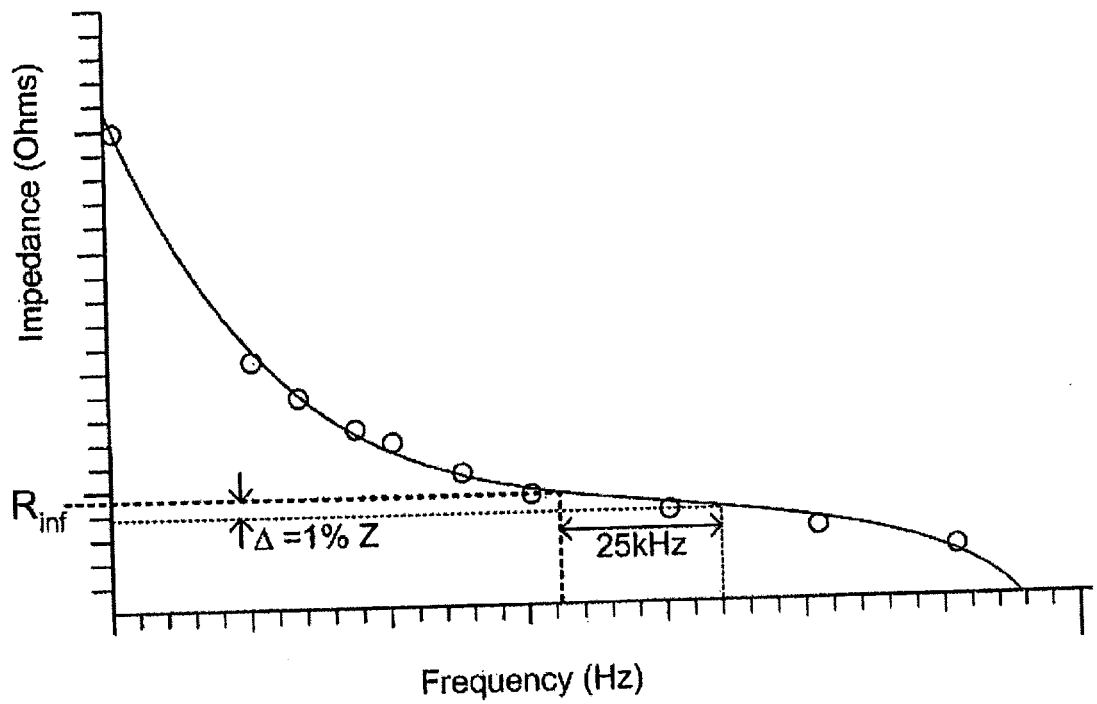
Figure 8:
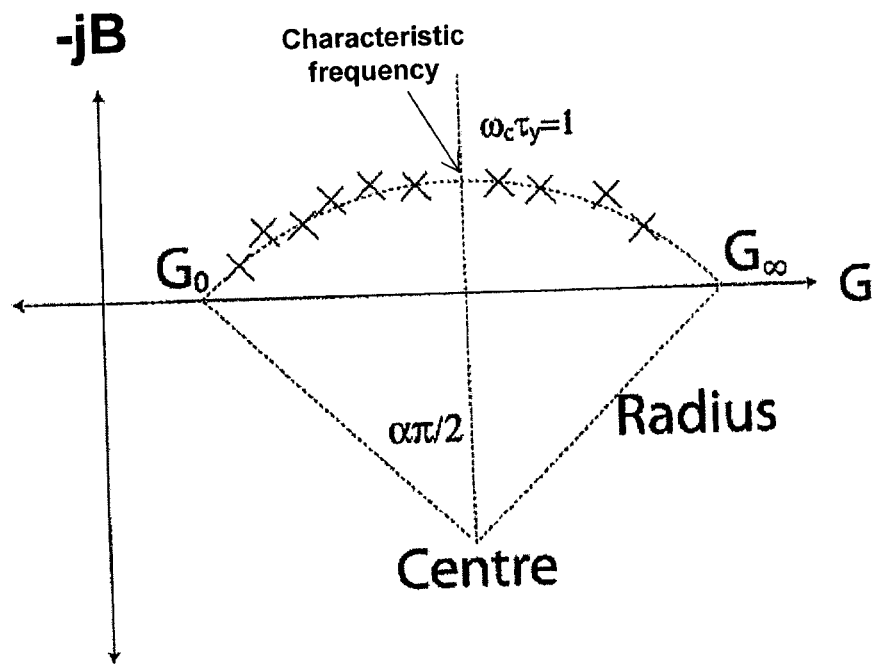

For example, in FIG. 6C, $R_{var}$ is determined iteratively by calculating instantaneous impedance values at a plurality of frequencies at each time point. FIGS. 10 and 11 describe an alternative method of determining a measure of cardiac function, by instead determining the characteristic frequency (stimulating at multiple frequencies) and using this characteristic frequency to determine the instantaneous impedance (or components of the instantaneous impedance). The step of determining a characteristic frequency may be performed only once during a cardiac cycle, or only periodically during a cardiac cycle, rather than at each time point $t_i$.

FIG. 10 is a schematic flowchart further illustrating one method of determining a measure of cardiac function in a subject. First, a characteristic frequency for the subject 1001 is determined. As previously described, the characteristic frequency may be determined by applying an electrical signal (or signals) having a plurality of frequencies to the subject, receiving the response signal(s) from the subject, and determining an instantaneous impedance value (or a component of the impedance) at each of the plurality of frequencies, fitting the values to a function (e.g., a frequency dependent function), and determining the characteristic frequency using the function. Any appropriate range of frequencies may be used, including frequencies between 2 and 10,000 kHz (e.g., 2-200 kHz, etc.), and any appropriate number of frequencies may be used (e.g., 2, 8, 16, 50, 100, etc.). Although the instantaneous impedance values may be determined at each time point, in some variations components of the instantaneous impedance values (e.g., reactance and/or resistance) are determined at each time point, rather than the combined impedance value. In some variations, phase is used.

Next, the impedance, or a component of the impedance, can be determined at different time points during all or part of a cardiac cycle 1003. As described above, the intracellular resistance may be calculated from the impedance. In some variations the reactance component of the impedance is determined at different time points of a cardiac cycle by applying electrical signals at the characteristic frequency. Thus, at least one reactance time point may be determined at that characteristic frequency. This reactance time point may be referred to as an instantaneous reactance at that time point. In some variations the component of the impedance determined at each time point using the characteristic frequency is phase, magnitude (or both). In some variations the instantaneous impedance is determined using the characteristic frequency at each time point.

In FIG. 10, the impedance (or a component of the impedance) at the characteristic frequency is determined at discrete time points during a complete cardiac cycle 1005. Any number of time points within the cardiac cycle may be taken (e.g., the number of sample points within the cardiac cycle). Although most of the methods described herein take measurements over a full cardiac cycle, a portion of a cardiac cycle or multiple cardiac cycles may also be used. As briefly mentioned above, these instantaneous values determined during the cardiac cycle using the characteristic frequency may be stored for use in determining a cardiac function such as stroke volume or cardiac output.

As mentioned above, a new characteristic frequency may be determined during the cardiac cycle, as indicated by the dashed line 1011 in FIG. 10. For example, a new characteristic frequency may be determined for each time point, or for some subset of time points.

Finally, a measure of cardiac function may be determined using the instantaneous impedance (or a component of impedance) value(s) determined at the characteristic frequency 1007 in the previous steps. For example, the instantaneous impedance values measured at the characteristic frequency may be used to determine a stroke volume and/or cardiac output. The maximum change in impedance, $(dz/dt)_{max}$, is proportional to the stroke volume and also to the cardiac output. For example, stroke volume may be represented as:

$$SV = \frac{L'^3 \left(\frac{dz}{dt}\right)_{max} VET}{Z_B}$$

where: SV=stroke volume, $(dz/dt)_{max}$=maximum rate of change in measured impedance at the beginning of systolic cycle, VET=left ventricular ejection time, and L'=thoracic length estimated from the subject's height and weight using a nomogram. L' also accounts for blood resistivity. $Z_B$ is a baseline impedance value. Thus, the constants may be combined, expressing the stroke volume in terms of elements (e.g., $(dz/dt)_{max}$) that may be determined for each cardiac cycle. Cardiac output is related to stroke volume (e.g., cardiac output=SV*heart rate).

In one example, the instantaneous reactance at the characteristic frequency may be used to determine a measure of cardiac function. For example, the instantaneous reactance at the characteristic frequency can be measured at each sample point during a cardiac cycle by stimulating the subject at the characteristic frequency. The change in the reactance $(dX/dt)_{max}$ is also proportional to the stroke volume and the cardiac output, and may therefore be used (in conjunction with appropriate monograms) to determine these measures of cardiac function. FIG. 11 illustrates this exemplary method.

A system for analyzing cardiac function in a subject may include any of the elements described above, and may also include one or more processors for executing the procedures described herein. For example, a system may include a processor (e.g., microprocessor) for controlling the application of an electrical signal having a plurality of frequencies to the subject 1101. Thus, the processor may be connected to a signal generator and electrodes to be connected to the subject for stimulation. The controller may also be connected to electrodes for receiving an electrical signal from the subject in response to the applied signal 1103. The input signal may also be sent to the controller, and both the input and output signals may be digitized, filtered, or otherwise conditioned. The processor may further determine a characteristic frequency by comparing the applied and received electrical signals 1105, as described above.

The characteristic frequency may then be used to determine an instantaneous reactance, or any other appropriate characteristic of impedance, including phase 1107. For example, the system may detect the relative phase shift (dφ/dt) between the injected signal and the response signal at discrete times during a full cardiac cycle or a portion of a cardiac cycle by applying an electrical signal at the determined characteristic frequency and comparing the phase of the response signal to the applied signal. As mentioned above, in some variations, the characteristic frequency may be determined once during the cardiac cycle (e.g., at the start of the measurement), or a new characteristic frequency may be determined before determining the component of the impedance (e.g., reactance or phase shift) at each time point, as indicated by the dashed line 1117 in FIG. 11. In some variations, a new characteristic frequency may be recalculated after some number of data point (or a fraction of the cardiac cycle).

These instantaneous impedance values determined at the characteristic frequency (e.g., the instantaneous impedance, instantaneous reactance, instantaneous phase shift, etc.) may be stored by the system. For example, the processor may include a memory to store these values. In some variations all of the values are not stored, but only a running value (e.g., the maximum value, a sum of the values, a product of the values, etc.) is stored. These stored values may be used to determine a measure of cardiac function 1111. For example, the phase shift (dφ/dt) values may be used to determine stroke volume and/or cardiac output. For example, the phase shift may be proportional to the changes in blood flow in the aorta, as previously described. Thus, the stroke volume may be expressed as:

$$SV = C'^{*}(d\phi/dt)_{max}*VET$$

where VET is ventricular ejection time, and C' is a constant that may be based on individual patient characteristics (including height, weight, gender, age, etc.). As previously described, the VET may be determined for each cardiac cycle. For example, the ECG may be used to determine the length of each heart beat, as well as the start of ejection and the end of ejection, from which VET can be estimated. Heart rate (and therefore cardiac output) may also be determined from the phase information.

The measure of cardiac function determined may be displayed, stored or transmitted. Thus, any of the systems for analyzing cardiac function described herein may include a display (e.g., screen, printer, etc.) or telemetry (wireless, LAN, etc.), or the like. The systems described herein may also include one or more inputs such as keyboards, mouse, touch screen, etc. for inputting subject information.

Persons skilled in the art will appreciate that numerous variations and modifications will become apparent. All such variations and modifications which become apparent to persons skilled in the art, should be considered to fall within the spirit and scope that the invention broadly appearing before described.

What is claimed is:

1. A method of determining a measure of cardiac function in a subject, the method comprising:
    (a) determining a characteristic frequency for the subject, wherein the characteristic frequency is the most negative reactance within an applied frequency range;
    (b) determining the impedance phase angle at the characteristic frequency; and
    (c) determining a measure of cardiac function using the impedance phase angle determined solely at the characteristic frequency and displaying, storing, or transmitting the measure of cardiac function.

2. The method of claim 1, wherein the characteristic frequency of the subject is determined by:
    (a) applying an electrical signal having a plurality of frequencies to the subject;
    (b) determining an instantaneous impedance value at each of the plurality of frequencies;
    (c) fitting the instantaneous impedance values to a frequency dependent function; and
    (d) determining the characteristic frequency using the function.

3. The method of claim 2, wherein the characteristic frequency is determined from an approximate maximum of the function.

4. The method of claim 2, wherein the frequency dependent function is a function based on a Wessel plot or a Cole plot.

5. The method of claim 2, wherein the frequency dependent function is a polynomial curve fit.

6. The method of claim 1, wherein the characteristic frequency is determined by applying one or more electrical signal having frequencies within the range of 2-10,000 kHz to the subject.

7. The method of claim 1, wherein the impedance phase angle at the characteristic frequency is determined by comparing an electrical signal applied to the subject having a frequency at approximately the characteristic frequency to an electrical signal received from the subject in response to the applied electrical signal.

8. The method of claim 1, wherein the step of determining the impedance phase angle at the characteristic frequency comprises determining an instantaneous reactance.

9. The method of claim 1, wherein the step of determining the impedance phase angle at the characteristic frequency comprises determining an instantaneous phase shift.

10. The method of claim 1, wherein a stroke volume is determined as the measure of cardiac function.

11. The method of claim 10, wherein the stroke volume is determined by multiplying the maximum change in reactance during a cardiac cycle by one or more constants including constants based on the subject's physical characteristics.

12. The method of claim 1, wherein a cardiac output is determined as the measure of cardiac function.

13. The method of claim 1, wherein the measure of cardiac function is determined by determining the phase angle at the characteristic frequency for a number of sequential time points during a cardiac cycle.

14. The method of claim 1, wherein the measure of cardiac function is determined by determining the reactance at the characteristic frequency for a number of sequential time points during a cardiac cycle.

15. The method of claim 1, wherein the measure of cardiac function is determined by determining the characteristic frequency and the phase angle at the characteristic frequency for a number of sequential time points during a cardiac cycle.

16. A method of determining a measure of cardiac function in a subject, the method comprising:
    (a) applying an electrical signal having a plurality of frequencies to the subject;
    (b) receiving an electrical signal from the subject in response to the applied signal;
    (d) determining a characteristic frequency for the subject by comparing the applied and received electrical signals, wherein the characteristic frequency is the most negative reactance within an applied frequency range;
    (c) determining the impedance phase angle at substantially the characteristic frequency; and
    (d) determining a measure of cardiac function using the impedance phase angle determined solely at the characteristic frequency and displaying, storing, or transmitting the measure of cardiac function.

17. The method of claim 16, further wherein the characteristic frequency is determined by comparing the applied and received electrical signals to determine an instantaneous impedance value and fitting the instantaneous impedance values to a frequency dependent function.

18. The method of claim 16, wherein the measure of cardiac function is selected from the group consisting of: stroke volume and cardiac output.

19. The method of claim 16, wherein the measure of cardiac function is determined by determining the phase shift at the characteristic frequency for a number of sequential time points during a cardiac cycle.

20. A system for analyzing cardiac function in a subject, the device comprising:
    a plurality of electrodes configured to be attached to a subject; and
    a processor connected to the plurality of electrodes, the processor configured to execute processing logic, the processing logic configured to:
    (a) control the application of an electrical signal having a plurality of frequencies to the subject;
    (b) receive an electrical signal from the subject in response to the applied signal;
    (c) determine a characteristic frequency by comparing the applied and received electrical signals, wherein the characteristic frequency is the most negative reactance within an applied frequency range;

(d) determine the impedance phase angle at the characteristic frequency; and
(e) determine a measure of cardiac function using the impedance phase angle determined solely at the characteristic frequency.

21. The system of claim 20, further comprising a signal generator coupled to processor for generating the electrical signals applied to the subject.

22. The system of claim 20, further comprising one or more sensors for detecting the electrical signals from the subject in response to the applied electrical signals.

23. The system of claim 20, further comprising processing logic for determining the measure of cardiac function by multiplying the impedance phase angle by one or more constants including constants based on the subject's physical characteristics.

24. The system of claim 20, further comprising an input device in communication with the processor for entering at least some of the subject's physical characteristics.

* * * * *

UNITED STATES PATENT AND TRADEMARK OFFICE
CERTIFICATE OF CORRECTION

PATENT NO. : 8,068,906 B2
APPLICATION NO. : 11/776456
DATED : November 29, 2011
INVENTOR(S) : Scott Matthew Chetham It is certified that error appears in the above-identified patent and that said Letters Patent is hereby corrected as shown below:

In the Drawings

Please replace Figs. 3A, 3B, 4, 5, 7 and 8 with the attached.

In the Specification

Column 5, line 59; after "resistance" and before "of the", delete "$R_1$" and insert --$R_I$--.

Column 5, line 62; after "resistance", delete "$R_T$" and insert --$R_I$--.

Column 5, line 64; before "and then using", delete "$R_o$ and $R_\infty$," and insert --$R_0$ and $R_\infty$,--.

Column 6, line 21; delete "$Y_{CPE} = (\omega\tau)^m(G_{m\tau=1} + jB_{\omega\tau=1})$" and insert --$Y_{CPE} = (\omega\tau)^m(G_{\omega\tau=1} + jB_{\omega\tau=1})$--.

Column 6, line 30; before "is the phase of", delete "$\phi_{cpe}$", and insert --$\varphi_{cpe}$--.

Column 6, line 43; after "time constant" and before "will", delete "$\tau_r$" and insert --$\tau_Z$--.

Column 6, line 56; after "script" and before "is used", delete "m" and insert --*m*--.

Column 9, line 25; after "from" and before "using the", delete "$R_o$ and $R_\infty$" and insert --$R_0$ and $R_\infty$--.

Column 9, line 33; before "can be determined" delete "$R_\infty$" and insert --$R_\infty$--.

Column 9, line 40; after "is identified as" and before "and", delete "$R_\infty$" and insert --$R_\infty$--.

Column 9, line 54; after "at the" and before "impedance)", delete "character" and insert --characteristic--.

Column 9, line 64; after "locus from" and before "By comparing", delete "$R_o$ to $R_\infty$." and insert --$R_0$ to $R_\infty$.--.

Column 10, line 8; after "either" and before "or the characteristic", delete "$R_o$ to $R_\infty$," insert --$R_0$ to $R_\infty$,--.

Column 10, line 12; after "values of" and before "or the", delete "$R_o$, $R_\infty$," and insert --$R_0$, $R_\infty$,--.

Signed and Sealed this
Twelfth Day of November, 2013

Teresa Stanek Rea
*Deputy Director of the United States Patent and Trademark Office*

CERTIFICATE OF CORRECTION (continued)
U.S. Pat. No. 8,068,906 B2

Column 10, line 13; after "impedance" and before "the equation", delete "$Z_o$," and insert --$Z_c$,--.

Column 11, line 58; before "are optional" delete "n (range ... 4>n<4) and m (range ... 4>m<4)" and insert --n (range ... -4>n<4) and m (range ... -4>m<4)--.

Column 13, line 29; after "component of" and before "impedance" delete "the".

Column 14, line 20; after "appropriate" and before "to determine" delete "monograms)" and insert --nomograms)--.

Column 14, lines 42-43; after "phase shift" and before "between the", delete "(dφ/dt)" and insert --(dφ/dt)--.

Column 14, line 66; after "shift" and before "values", delete "(dφ/dt)" and insert --(dφ/dt)--.

Column 15, line 5; delete "SV= C'*(dφ/dt)$_{max}$*VET" and insert --SV= C' *(dφ/dt)$_{max}$*VET--.

In the Claims

Claim 16, column 16, line 33; delete "(d)" and insert --(c)--.

Claim 16, column 16, line 37; delete "(c)" and insert --(d)--.

Claim 16, column 16, line 39; delete "(d)" and insert --(e)--.

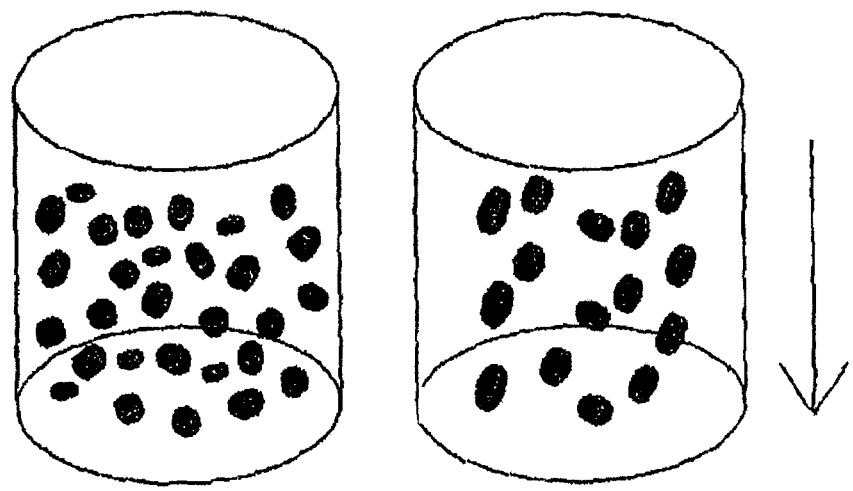
FIG. 3A         FIG. 3B
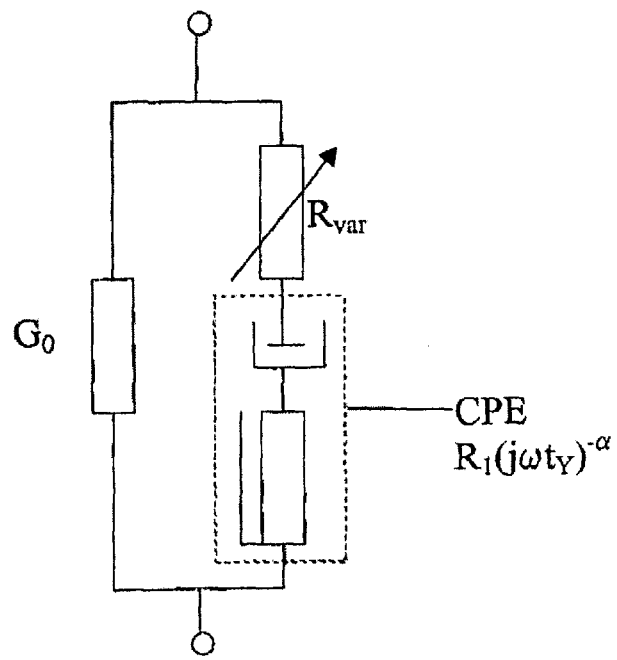
FIG. 4